(12) United States Patent
Howard et al.

(10) Patent No.: US 8,487,092 B2
(45) Date of Patent: Jul. 16, 2013

(54) PYRROLOBENZODIAZEPINES

(75) Inventors: Philip Wilson Howard, London (GB);
Stephen John Gregson, London (GB);
ZhiZhi Chen, London (GB); Arnaud Charles Tiberghien, London (GB);
Luke Masterson, London (GB)

(73) Assignee: Spirogen Developments SARL, St-Legier-La Chiesaz (CH)

( * ) Notice: Subject to any disclaimer, the term of this patent is extended or adjusted under 35 U.S.C. 154(b) by 3 days.

(21) Appl. No.: 13/124,232

(22) PCT Filed: Oct. 16, 2009

(86) PCT No.: PCT/GB2009/002495
§ 371 (c)(1),
(2), (4) Date: Apr. 14, 2011

(87) PCT Pub. No.: WO2010/043877
PCT Pub. Date: Apr. 22, 2010

(65) Prior Publication Data
US 2011/0201803 A1 Aug. 18, 2011

(30) Foreign Application Priority Data
Oct. 17, 2008 (GB) .................................. 0819097.7

(51) Int. Cl.
*C07D 519/00* (2006.01)
(52) U.S. Cl.
USPC ........................................................ 540/496
(58) Field of Classification Search
USPC ........................................................ 540/496
See application file for complete search history.

(56) References Cited

U.S. PATENT DOCUMENTS

| 6,660,856 | B2 | 12/2003 | Wang |
| 2007/0185336 | A1 | 8/2007 | Rossen et al. |

FOREIGN PATENT DOCUMENTS

| JP | 58180487 | 10/1983 |
| WO | 95/04718 | 2/1995 |
| WO | 00/12508 | 3/2000 |
| WO | 2004/043963 | 5/2004 |
| WO | 2005/042535 | 5/2005 |
| WO | 2005/085251 | 9/2005 |
| WO | 2005/085259 | 9/2005 |
| WO | 2006/111759 | 10/2006 |
| WO | 2007/085930 | 8/2007 |

OTHER PUBLICATIONS

Antonow et al., "Parallel synthesis of a novel C2-aryl pyrrolo[2,1-c][1,4] benzodiazepine (PBD) library," J. Comb. Chem. (2007) 9:437-445.
Arima et al., "Studies on Tomaymycin, a New Antibiotic. I. Isolation and Properties of Tomaymycin," J. Antibiotics (1972) 25:437-444.
Bose et al., "New Approaches to Pyrrolo[2,1-c][1,4]benzodiazepines: Synthesis, DNA-binding and cytotoxicity of DC-81," Tetrahedron, 48, 751-758 (1992).
Cooper, N., "Design, synthesis and evaluation of novel C2-aryl pyrrolobenzodiazepines as potential anticancer agents," Thesis submitted to School of Pharmacy, University of London, (Oct. 5, 2006).
Fey, T. et al., "Silica-supported TEMPO catalysts: synthesis and application in the Anelli oxidation of alcohols," J. Org. Chem. (2001) 66:8154-8159.
Gregson, S. et al., "Synthesis of a novel C2/C2'-exo unsaturated pyrrolobenzodiazepine cross-linking agent with remarkable DNA binding affinity and cytotoxicity," Chemical Communications, 797-798 (1999).
Gregson, S.J. et al., "Linker length modulates DNA cross-linking reactivity and cytotoxic potency of C8/C8' ether-linked C2-exo-unsaturated pyrrolo[2,1-c][1,4]benzodiazepine (PBD) dimers," J. Med. Chem. (2004) 1161-1174.
Hara et al., "DC 102, a new glycosidic pyrrolo(1,4)benzodiazepine antibiotic produced by *Streptomyces* sp.", J. Antibiotics, 41, 702-704 (1988).

(Continued)

*Primary Examiner* — Bruck Kifle
(74) *Attorney, Agent, or Firm* — Michael Best & Friedrich LLP

(57) ABSTRACT

The invention relates to certain pyrrolobenzodiazepines (PBDs), and in particular pyrrolobenzodiazepine dimers bearing C2 substitutions, including compounds of formula (T): wherein: $R^2$ is $CHR^{2A}$, and $R^{2A}$ is independently selected from H, R, $CO_2R$, COR, CHO, $CO_2H$, and halo; $R^6$ and $R^9$ are independently selected from H, R, OH, OR, SH, SR, $NH_2$, NHR, NRR', $NO_2$, $Me_3Sn$ and halo; $R^7$ is independently selected from H, R, OH, OR, SH, SR, $NH_2$, NHR, NRR', $NO_2$, $Me_3Sn$ and halo; $R^8$ is independently selected from H, R, OH, OR, SH, SR, $NH_2$, NHR, NRR', $NO_2$, $Me_3Sn$ and halo; R is independently selected from optionally substituted $C_{1-12}$ alkyl, $C_{3-20}$ heterocyclyl and $C_{5-20}$ aryl groups; or the compound is a dimer with each monomer being of formula (M), where the $R^7$ groups or $R^8$ groups of each monomer form together a dimer bridge having the formula —X—R"—X— linking the monomers; wherein R" is a $C_{3-12}$ alkylene group, which chain may be interrupted by one or more heteroatoms, e.g. O, S, N(H), and/or aromatic rings, e.g. benzene or pyridine; and each X is independently selected from O, S, or N(H); or any pair of adjacent groups from $R^6$ to $R^9$ together form a group —O—$(CH_2)_p$—O—, where p is 1 or 2, and salts and solvates thereof, and their use as intermediates for the preparation of other PBD compounds.

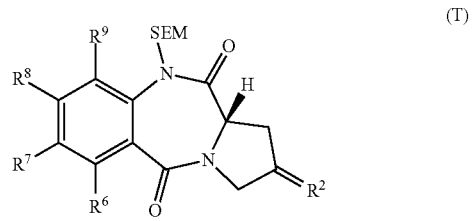

(T)

23 Claims, No Drawings

OTHER PUBLICATIONS

Hochlowski, J. et al., "Abbeymycin, a new anthramycin-type antibiotic produced by a streptomycete," J. Antibiotics, 40, 145-148 (1987).

Hurley, L. and Needham-Vandevanter, D., "Covalent Binding of Antitumor Antibiotics in the Minor Groove of DNA. Mechanism of Action of CC-1065 and the Pyrrolo(1,4)benzodiazepines," Acc. Chem. Res., 19, 230-237 (1986).

Itoh et al., "Sibanomicin, a new pyrrolo(1,4)benzodiazepine antitumor antibiotic produced by a *Micromonospora* sp." J. Antibiotics, 41, 1281-1284 (1988).

Kohn, K., "Anthramycin," Antibiotics III, Springer-Verlag, NY, 3-11 (1975).

Konishi, M. et al., "Chicamycin, a new antitumor antibiotic II. Structure determination of chicamycins A and B," J. Antibiotics, 37, 200-206 (1984).

Kunimoto et al., "Mazethramycin, a new member of anthramycin group antibiotics," J. Antibiotics, 33, 665-667 (1980).

Langley, D.R. and Thurston, D.E., "A versatile and efficient synthesis of carbinolamine-containing pyrrolo[1,4] benzodiazepines via the cyclization of N-92-aminobenzoyl)pyrrolidine-2-carboxaldehyde diethyl thioacetals: total synthesis of prothracarcin," J. Org. Chem., 52, 91-97 (1987).

Leber, J.D. et al., "A revised structure for sibiromycin," J. Am. Chem. Soc., 110, 2992-2993 (1988).

Leimgruber, W. et al., "Isolation and characterization of anthramycin, a new antitumor antibiotic," J. Am. Chem. Soc., 87, 5791-5793 (1965).

Leimgruber, W. et al., "The structure of anthramycin," J. Am. Chem. Soc., 87, 5793-5795 (1965).

Narukawa, Y., "General and efficient synthesis of 2-alkylcarbapenems synthesis of dethia carba analogs of clinically useful carbapenems via palladium-catalyzed cross-coupling reaction," Tetrahedron (1997) 53:539-556.

Shimizu, K et al., "Prothracarcin, a Novel Antitumor Antibiotic," J. Antibiotics (1982) 35:972-978.

Takeuchi, T. et al., "Neothramycins A and B, New Antitumor Antibiotics," J. Antibiotics, 29, 93-96 (1976).

Thurston, D.E. and Bose, D.S., "Synthesis of DNA-Interactive Pyrrolo[2,1-c][1,4]benzodiazepines," Chem. Rev., 94:433-465 (1994).

Thurston, D.E. and Thompson, A.S., "The molecular recognition of DNA," Chem. Brit., 26, 767-772 (1990).

Tozuka et al., "Studies on tomaymycin. II. Total synthesis of the antitumor antibiotics, E-and Z-tomaymycins," J. Antibiotics (Tokyo) (1983) 36:276-282.

Tsunakawa, M. et al., "Porothramycin, a new antibiotic of the anthramycin group: Production, isolation, structure and biological activity," J. Antibiotics, 41:1366-1373 (1988).

PYRROLOBENZODIAZEPINES

The present invention relates to pyrrolobenzodiazepines (PBDs), and in particular pyrrolobenzodiazepine dimers bearing C2 substitutions.

CROSS-REFERENCE TO RELATED APPLICATIONS

This patent application is a national stage filing under 35 U.S.C. 371 of International Application No. PCT/GB2009/002495, filed Oct. 16, 2009, which claims priority benefits to United Kingdom Patent Application No. 0819097.9, filed Oct. 17, 2008. These applications are incorporated herein by reference in their entireties.

BACKGROUND TO THE INVENTION

Some pyrrolobenzodiazepines (PBDs) have the ability to recognise and bond to specific sequences of DNA; the preferred sequence is PuGPu. The first PBD antitumour antibiotic, anthramycin, was discovered in 1965 (Leimgruber, et al., *J. Am. Chem. Soc.*, 87, 5793-5795 (1965); Leimgruber, et al., *J. Am. Chem. Soc.*, 87, 5791-5793 (1965)). Since then, a number of naturally occurring PBDs have been reported, and over 10 synthetic routes have been developed to a variety of analogues (Thurston, et al., *Chem. Rev.* 1994, 433-465 (1994)). Family members include abbeymycin (Hochlowski, et al., *J. Antibiotics*, 40, 145-148 (1987)), chicamycin (Konishi, et al., *J. Antibiotics*, 37, 200-206 (1984)), DC-81 (Japanese Patent 58-180 487; Thurston, et al., *Chem. Brit.*, 26, 767-772 (1990); Bose, et al., *Tetrahedron*, 48, 751-758 (1992)), mazethramycin (Kuminoto, et al., *J. Antibiotics*, 33, 665-667 (1980)), neothramycins A and B (Takeuchi, et al., *J. Antibiotics*, 29, 93-96 (1976)), porothramycin (Tsunakawa, et al., *J. Antibiotics*, 41, 1366-1373 (1988)), prothracarcin (Shimizu, et al, *J. Antibiotics*, 29, 2492-2503 (1982); Langley and Thurston, *J. Org. Chem.*, 52, 91-97 (1987)), sibanomicin (DC-102)(Hara, et al., *J. Antibiotics*, 41, 702-704 (1988); Itoh, et al.,*J. Antibiotics*, 41, 1281-1284 (1988)), sibiromycin (Leber, et al., *J. Am. Chem. Soc.*, 110, 2992-2993 (1988)) and tomamycin (Arima, et al., *J. Antibiotics*, 25, 437-444 (1972)). PBDs are of the general structure:

They differ in the number, type and position of substituents, in both their aromatic A rings and pyrrolo C rings, and in the degree of saturation of the C ring. In the B-ring there is either an imine (N=C), a carbinolamine(NH—CH(OH)), or a carbinolamine methyl ether (NH—CH(OMe)) at the N10-C11 position which is the electrophilic centre responsible for alkylating DNA. All of the known natural products have an (S)-configuration at the chiral C11a position which provides them with a right-handed twist when viewed from the C ring towards the A ring. This gives them the appropriate three-dimensional shape for isohelicity with the minor groove of B-form DNA, leading to a snug fit at the binding site (Kohn, In *Antibiotics III*. Springer-Verlag, New York, pp. 3-11 (1975); Hurley and Needham-VanDevanter, *Acc. Chem. Res.*, 19, 230-237 (1986)). Their ability to form an adduct in the minor groove, enables them to interfere with DNA processing, hence their use as antitumour agents.

Dimeric pyrrolobenzodiazepines offer advantages over monomeric pyrrolobenzodiazepines in that they possess the ability to cross-link DNA in the minor groove, which can lead to an increase in cytotoxicity.

A particularly advantageous pyrrolobenzodiazepine compound is described by Gregson et al. (*Chem. Commun.* 1999, 797-798) as compound 1, and by Gregson et al. (*J. Med. Chem.* 2001, 44, 1161-1174) as compound 4a. This compound, also known as SJG-136, is shown below:

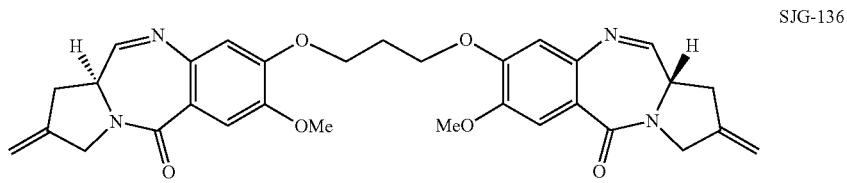

SJG-136

SJG-136 is also described in WO 00/12508 by some of the present inventors, and the corresponding bis-bisulfite adducts (such as SJG-720) are described in WO 2005/042535 by some of the present inventors.

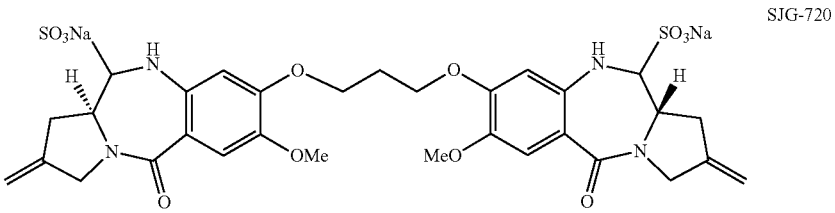

SJG-720

However, the present inventors have found difficulties with the syntheses of SJG-136 as described in the references cited above. For example, in WO 2006/111759 the synthesis comprised a very large number of steps, which decreased the potential yield as well as adding to the experimental difficulty of synthesising the product.

There is a need therefore for an improved method of preparing SJG-136, and also SJG-720, as well as related compounds, which has fewer steps and/or provides an increased yield of the final product.

SUMMARY OF THE INVENTION

In a general aspect the present invention provides novel intermediates for use in the preparation of compound (M):

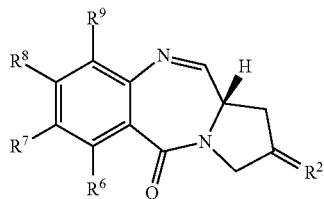

M wherein:

$R^2$ is $CHR^{2A}$, and $R^{2A}$ is independently selected from H, R, $CO_2R$, COR, CHO, $CO_2H$, and halo;

$R^6$ and $R^9$ are independently selected from H, R, OH, OR, SH, SR, $NH_2$, NHR, NRR', $NO_2$, $Me_3Sn$ and halo;

$R^7$ is independently selected from H, R, OH, OR, SH, SR, $NH_2$, NHR, NRR', $NO_2$, $Me_3Sn$ and halo;

$R^8$ is independently selected from H, R, OH, OR, SH, SR, $NH_2$, NHR, NRR', $NO_2$, $Me_3Sn$ and halo;

R is independently selected from optionally substituted $C_{1-12}$ alkyl, $C_{3-20}$ heterocyclyl and $C_{5-20}$ aryl groups;

or the compound is a dimer with each monomer being of formula (M), where the $R^7$ groups or $R^8$ groups of each monomer form together a dimer bridge having the formula —X—R"—X— linking the monomers;

wherein R" is a $C_{3-12}$ alkylene group, which chain may be interrupted by one or more heteroatoms, e.g. O, S, N(H), and/or aromatic rings, e.g. benzene or pyridine; and each X is independently selected from O, S, or N(H);

or any pair of adjacent groups from $R^6$ to $R^9$ together form a group —O—$(CH_2)_p$—O—, where p is 1 or 2, and salts and solvates thereof.

In a preferred embodiment, (M) is a compound of formula (A):

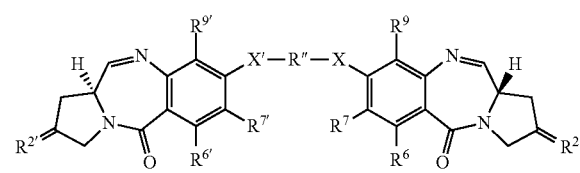

A wherein $R^{2'}$, $R^{6'}$, $R^{7'}$, $R^{9'}$, and X' are independently selected from the same groups as $R^2$, $R^6$, $R^7$, $R^9$, and X respectively.

In one embodiment, the present invention provides novel intermediates for use in the preparation of SJG-136 and the precursors thereof.

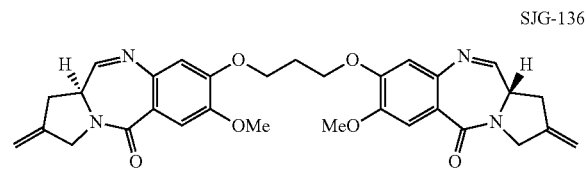

SJG-136

In one aspect of the invention there is provided a compound of formula (T):

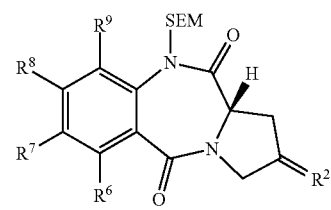

T wherein $R^2$, $R^6$, $R^7$, $R^8$, and $R^9$ are as defined according to the compounds of formula (M), and salts and solvates thereof. (T) finds use as a precursor in processes for the preparation of (M).

In a preferred embodiment, (T) is a compound of formula (S):

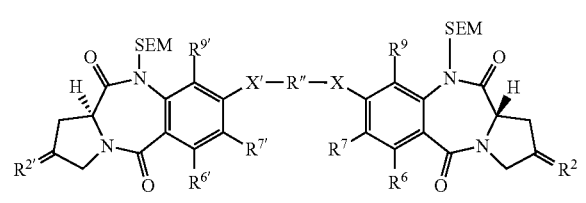

S wherein $R^{2'}$, $R^{6'}$, $R^{7'}$, $R^{9'}$, and X' are independently selected from the same groups as $R^2$, $R^6$, $R^7$, $R^9$, and X respectively.

In one embodiment. (T) is compound (8):

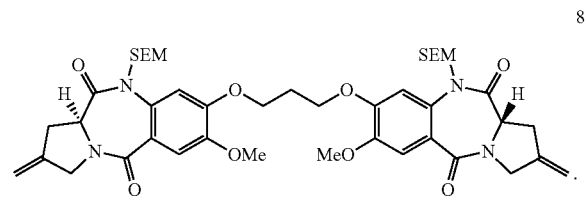

8

In one aspect of the invention there is provided a compound of formula (O):

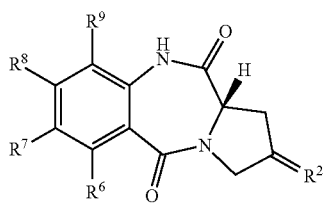

wherein $R^2$, $R^6$, $R^7$, $R^8$, and $R^9$ are as defined according to the compounds of formula (M), and salts and solvates thereof. (O) finds use as a precursor in processes for the preparation of (M), preferably via (T), and processes for the preparation of (T).

In a preferred embodiment, (O) is a compound of formula (B):

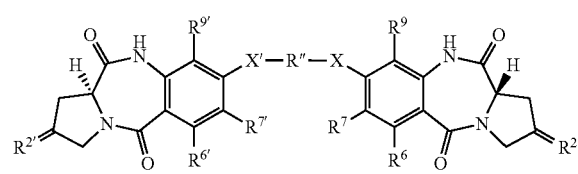

wherein $R^{2'}$, $R^{6'}$, $R^{7'}$, $R^{9'}$, and X' are independently selected from the same groups as $R^2$, $R^6$, $R^7$, $R^9$, and X respectively.

In one embodiment, (O) is compound (7):

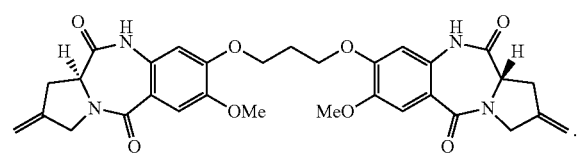

In one aspect, the present invention provides a process for the preparation of a compound of formula (M), the process comprising the step of reacting a compound of formula (T) with a reducing agent. In one embodiment, the process comprises the steps of reacting a compound of formula (T) with a reducing agent and then reacting the reduction product with silica or an organic acid.

In another aspect, the present invention provides a process for the preparation of a compound of formula (T), the process comprising the step of protecting the amide nitrogens of (O) with SEM.

In a further aspect, the present invention provides a process for the preparation of a compound formula (O), the process comprising the step of reacting a compound of formula (X) with a compound of formula (N), where (X) and (N) are:

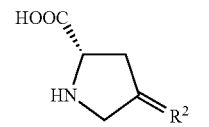

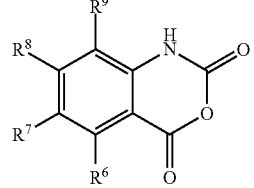

and $R^2$, $R^6$, $R^7$, $R^8$, and $R^9$ are as defined according to the compounds of formula (M).

In another aspect, the present invention provides a process for the preparation of a compound of formula (T), the process comprising the step of reacting (V) with a ylide comprising a group $R^2$ and/or $R^{2'}$, wherein (V) is:

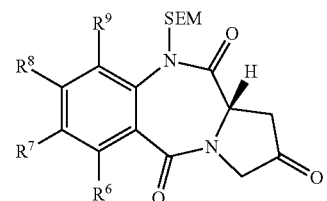

and $R^6$, $R^7$, $R^8$, and $R^9$ are as defined according to the compounds of formula (M).

In a preferred embodiment, (V) is a compound of formula (W):

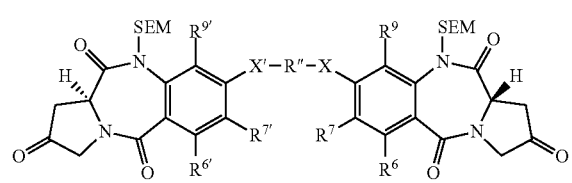

wherein $R^{6'}$, $R^{7'}$, $R^{9'}$, and X' are independently selected from the same groups as $R^6$, $R^7$, $R^9$, and X respectively.

In one aspect of the invention there is provided a process for preparing (M), the process comprising one or more of the processes of the invention, as described above.

In another aspect of the invention there is provided a process for preparing a compound of formula (P) from compound (M):

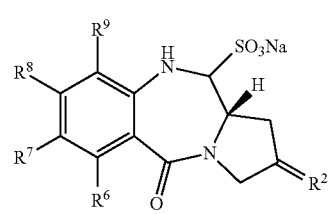

wherein $R^2$, $R^6$, $R^7$, $R^8$, and $R^9$ are as defined according to the compounds of formula (M).

DETAILED DESCRIPTION OF THE INVENTION

The present invention provides improved processes for the synthesis of SJG-136 and its analogues. The invention also provides novel intermediates for use in such processes. These methods allow SJG-136 to be prepared in higher yield and in less time compared to the processes that have been previously described for the preparation of this compound. The methods of the invention may also be used to prepare SJG-720 via SJG-136. The methods have general applicability to the preparation of compounds of formula (M) and (P).

Compounds (M), (N), (O) and (X)

The present invention provides methods for the preparation of compounds of formula (M) and compounds of formula (O), and also compounds of formula (T).

In one embodiment of the invention there is provided the use of a compound of formula (X) in a process for the preparation of a compound of formula (M) or a compound of formula (O).

In one embodiment, the compound of formula (M) is prepared by the reaction of compound (N) with compound (X). This reaction may be referred to as the coupling of partner (X) with partner (N).

The invention also provides the use of compounds (X) and (N) in processes for the preparation of compounds (T) and (P), as described below.

The preferred synthesis of compound (M) using compound (X) is shown in Scheme 1 below. Typically, compound (X) is coupled with compound (N) to form compound (O). The amide nitrogen atom of compound (O) is then protected with a SEM group to give compound (T), which may then be converted to compound (M). If required, compound (M) may be reacted with a bisulfite salt to yield compound (P).

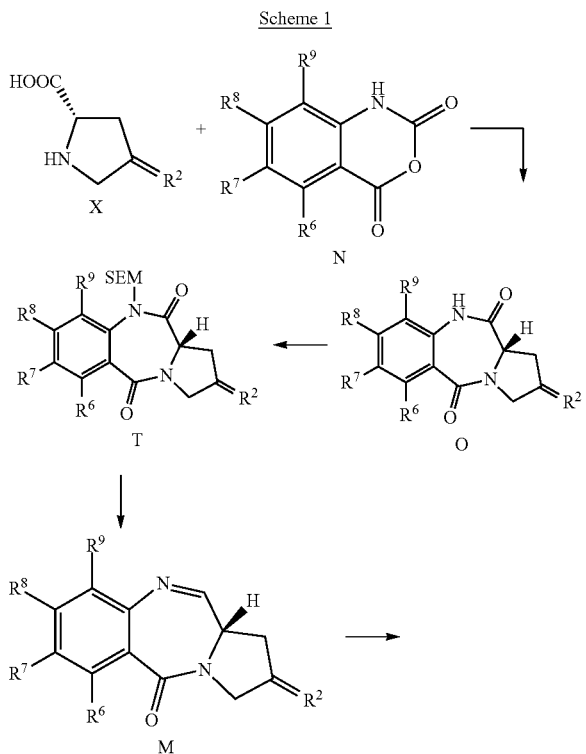

Scheme 1

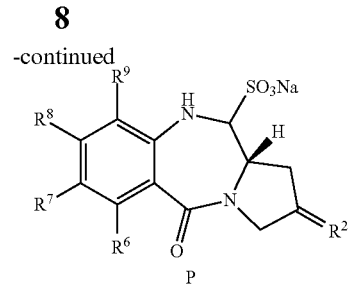

-continued

P

Compound (X) may be referred to as a C-ring coupling partner as it is the source of the C-ring in the PBD target molecule. Compound (N) may be referred to as an A-ring coupling partner as it is the source of the A-ring in the PBD target molecule. A coupling-partner is that compound which is used in a coupling reaction to, at least, link an A-ring source and a C-ring source together.

The inventors have established that compounds of formula (M) may be obtained in greater yield, in fewer steps and in less time compared to the methods that have been previously described in the art. In particular, the inventors have established that compound (A), a preferred structure of compound (M), may be obtained in greater yield, in fewer steps and in less time compared to the methods that have been previously described in the art.

The inventors have found that the proline-based compound of formula (X) may be used as a source for the C-ring in a PBD structure, such as compound (M) or compound (O). Advantageously, compound (X) includes the substituent that will later form the C2 substituent in the C-ring of the PBD target structure. Consequently, once the A- and C-rings have been joined, and the B-ring formed, no modification need be made at the PBD C2 position because the functionality here has been "pre-installed". This approach may be referred to as a convergent approach to PBD synthesis.

Many of the previous approaches to the synthesis of compounds of formula (M), and in particular compounds of general formula (A), have introduced the required C2 substituent at a later stage of the synthesis. The methods described in the art typically involve the connection of the A- and C-rings followed later, as a separate step, by formation of the B-ring. In one approach, such as described in Gregson at al. (*J. Med. Chem.* 2001, 44, 1161-1174), the substituent required at the C2 position is introduced after the A- and C-rings are connected. The B-ring is then formed at a later stage in the synthesis. This approach, which may be generally referred to as a linear approach, requires the introduction of a C2 substituent at a later stage of the synthesis, which may be synthetically complicated. Furthermore, the convergent approach may allow compounds (M) and (O) to be prepared in higher yield compared to a linear approach.

However, in the linear synthesis, between the introduction of the required C2 substituent and the formation of the B-ring, a number of functional group transformations must be performed, such as protecting group addition and removal. These steps add to the overall complexity and length of the synthesis.

The uses and methods of the present invention have further advantages which are not taught in the art. The present inventors have found that compound (X) may be used to prepare a PBD compound of formula (O) in one step. This step links the A- and C-rings together at the same time as the B-ring is formed. Previous approaches to the preparation of the B-ring of the PBD compound have proceeded in a greater number of steps, typically comprising the step of joining the A- and C-rings, undertaking a functional group transformation (including the removal of protecting groups), followed then by the formation of the B-ring. Thus, the present invention provides a route to compounds (M) and (O) that reduces the complexity and length of the overall synthesis.

Compound (O) may be converted to compound (M). In one embodiment, compound (O) is converted to compound (M) via compound (T):

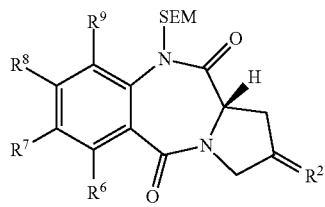

T wherein $R^2$, $R^6$, $R^7$, $R^8$, and $R^9$ are as defined according to the compounds of formula (O).

Compound (T) is provided as a useful precursor in processes for the preparation of compounds (M) and (P). The present invention also provides processes for the preparation of (T). The inventors have established that compound (T), which includes a SEM protecting group, may be used to access compound (M) in good yield and with excellent reproducibility. Compound (T) also finds use as a common intermediate in the linear and convergent strategies described herein.

Compound (T) may be prepared from compound (O) by protecting the amide nitrogen atoms of compound (O) with SEM. Compound (O) may be reacted with a SEM halide, for example SEM-Cl. A base may be used. The base may be n-BuLi.

In one embodiment, compound (T) is a compound of formula (S), as described above.

In one embodiment, compound (S) is compound (8), as described above.

Compound (M) may be prepared from compound (T). Preferably compound (T) is reacted with a reducing agent. The reducing agent may be a borohydride salt. Preferably the reducing agent is lithium borohydride. Alternatively, the reducing agent is sodium borohydride.

After treatment with the reducing agent, the product of the reduction may be treated with silica or an organic acid, such as citric acid or formic acid, thereby to yield (M).

The inventors have found that the compound (X) is particularly suitable as a building block in the synthesis of PBD compounds, as compound (X) allows compounds (M) and (O) to be prepared by a convergent synthesis approach and, additionally, allows the A- and C-rings to be linked at the same time as the B-ring is formed.

Compound (X), which comprises a C-ring source, is reacted with a suitably activated coupling partner comprising an A-ring source. A suitably activated coupling partner is compound (N). In a preferred embodiment, compound (N) is compound (C):

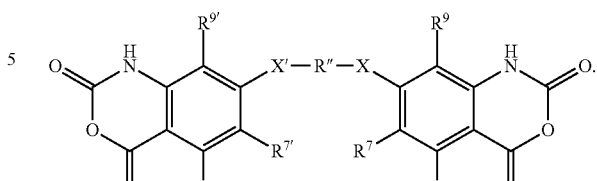

C

In a preferred embodiment, compound (C) is compound (6):

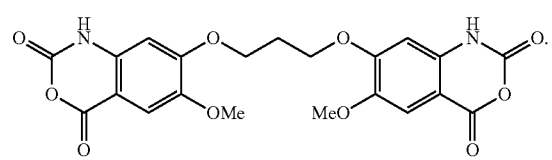

6

In other aspects of the invention there is provided the use of compound (N) in a process for the preparation of compound (M) or compound (O). It is preferred that compound (N) is reacted with compound (X).

Thus, in some aspects, the present invention combines the advantages of a convergent synthesis with a novel, combined A- and C-ring linking and B-ring forming step.

Compound (X) is an alternative proline-based coupling partner to those proline-based compounds that have been previously reported for use in the synthesis of PBD compounds. The use of compound (X) is particularly advantageous as it requires very few steps to prepare. From commercially available Boc-protected trans-4-hydroxy-L-proline (compound (1)), compound (X) may be prepared in only two steps via compound (2), as described herein.

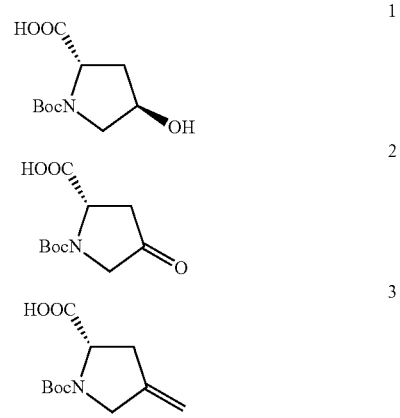

Compound (2) may be treated with an appropriate alkene-forming reagent, such as a Wittig-type reagent, to give, after an acid work up, compound (X), including for example compound (3). Suitable alkene-forming reagents are well known to those of skill in the art.

Some of the proline-based compounds previously reported in the art for use in the preparation of PBD compounds require multi-stage preparations. For example, WO 00/12508 discloses compound proline derivative (58) for use in the synthesis of PBD compounds. Compound (58) is coupled with an A-ring-containing partner.

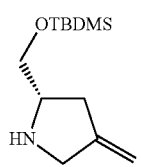

58

This compound is obtained in seven steps from commercially available trans-4-hydroxy-L-proline. In a series of examples, WO 00/12508 discloses the preparation of compound (58) from trans-4-hydroxy-L-proline (see examples 1(b) and 2(a)). The overall yield reported is 12%. In contrast, the present invention provides a C-ring coupling partner in two steps and 41% overall yield from a commercially available stating material.

WO 2007/085930 describes the preparation of dimer PBD-based compounds from a proline-derivative of formula (22). Compound (22) is coupled with an A-ring-containing partner. Compound (22) is produced in five steps from trans-4-hydroxy-L-proline (see example 13). The overall yield is not given. The present invention provides the C-ring coupling partner in fewer steps and in less time compared to the sequence described in WO 2007/085930.

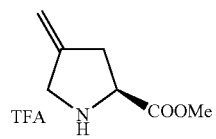

22

In one aspect, the invention provides compounds of formula (O) and compounds of formula (T).
In one embodiment, the compound of formula (M) is (A).
In one embodiment, the compound of formula (N) is (C).
In one embodiment, the compound of formula (O) is (B).
In one embodiment, the compound of formula (T) is (S).
In one embodiment, the compound of formula (X) is (3).
Compounds (A), (B), (C) and (O)
The present invention provides methods for the preparation of compounds of formula (A) compounds of formula (B), and also compounds of formula (O).
In one embodiment of the invention there is provided the use of a compound of formula (X) in a process for the preparation of a compound of formula (A). In one embodiment of the invention there is provided the use of a compound of formula (X) in a process for the preparation of a compound of formula (B).
In one embodiment, there is provided the use of a compound of formula (X) in a process for the preparation of a compound of formula (O). Compound (O) is typically formed from compound (A).
In a preferred embodiment, compound (A) is SJG-136. A preferred synthesis of SJG-136 using compound (3) is shown in Scheme 2 below. Typically, compound (3) is coupled with compound (6) to form compound (7). The amide nitrogen atom of compound (7) is then protected with a SEM group to give compound (8), which may then be converted to compound SJG-136. If required, SJG-136 may be reacted with a bisulfite salt to yield SJG-720.

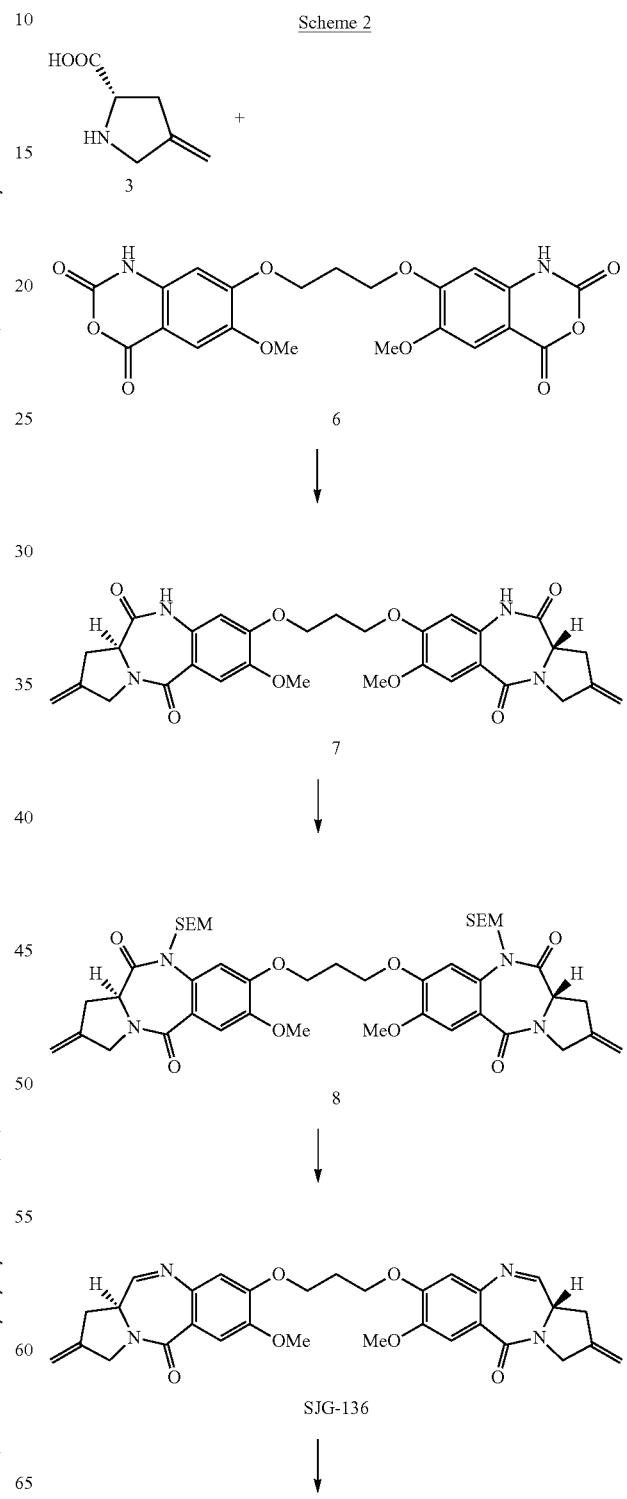

-continued

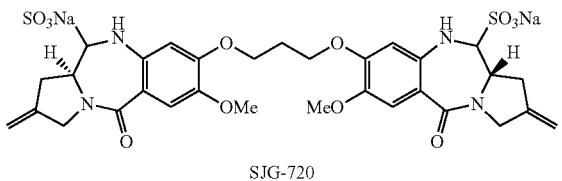

SJG-720

In one embodiment, the compound of formula (A) is prepared by the reaction of compound (C) with compound (X). This reaction may be referred to as the coupling of partner (X) with partner (C).

In another aspect of the invention there are provided compounds of formula (B).

In other embodiments of the invention there is provided the use of compound (C) in a process for the preparation of compound (A) or compound (B). It is preferred that compound (C) is reacted with compound (X).

In one embodiment, the compound of formula (A) is SJG-136.

In one embodiment, the compound of formula (B) is compound (7).

In one embodiment, the compound of formula (C) is compound (6).

In one embodiment, the compound of formula (X) is compound (3).

In one embodiment, compound (7) is prepared by reacting a compound of formula (3) with a compound of formula (6).

3

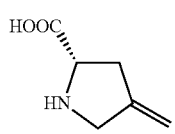

6

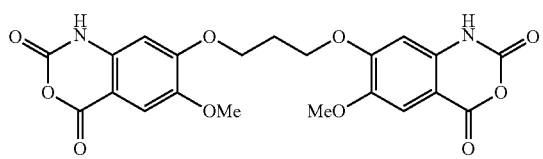

Compound (V)

The present invention provides the use of compounds of formula (V) in processes for the preparation of compounds of formula (T) and also of formula (M).

The synthesis of compound (M) from compound (V) is shown in Scheme 2a below. Typically, compound (V) is treated with an appropriate alkene-forming reagent, such as a Wittig-type reagent, to give compound (T). Suitable alkene-forming reagents are well known to those of skill in the art. In one embodiment, the alkene-forming reagent is a ylide comprising a group $R^2$. Compound (T) may then may then be converted to compound (M). If required, compound (M) may be reacted with a bisulfite salt to yield compound (P).

Scheme 2a

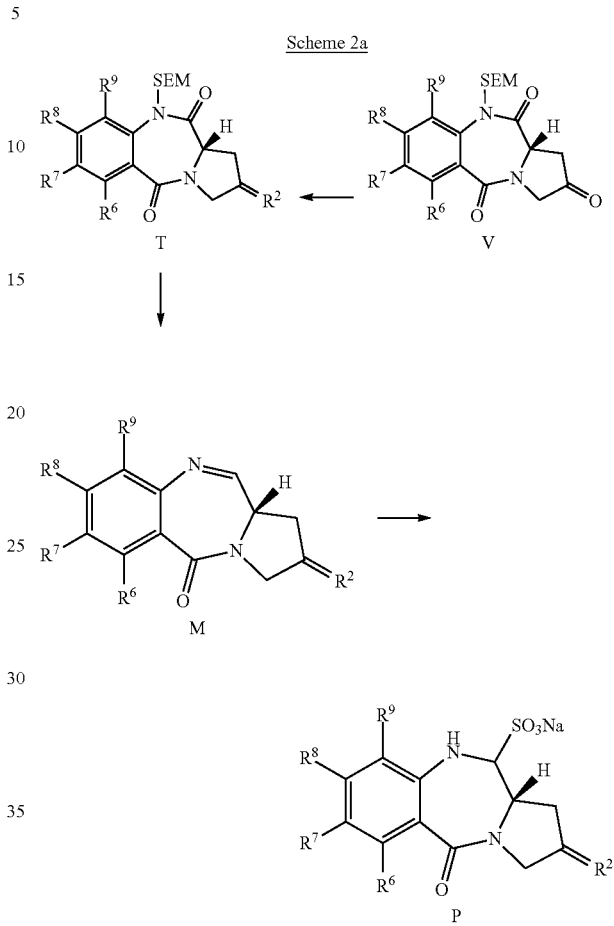

Compound (V) is reacted with an appropriate alkene-forming reagent to provide compound (T). Suitable alkene-forming reagents include Wittig reagents (such as ylides), the Tebbe reagent, and Horner-Wadsworth-Emmons reagents.

In one embodiment alkene-forming reagent is a ylide. The ylide may be a phosphonium methylene ylide, and the resulting product is a compound (V) where $R^2$ is $CH_2$. The phosphonium methylene ylide may be generated from methyltriphenylphosphonium halide and a base, such as a tert-butoxide salt. Preferably methyltriphenylphosphonium bromide is used in combination with potassium tert-butoxide. Alternative products of formula (V), where $R^2$ is other than $CH_2$, may be prepared using the appropriate ylide form, as is known to a person of skill in the art, or using alternative reagents, such as those discussed above.

Preferably the base used in the ylide forming step is freshly prepared. The methyltriphenylphosphonium halide is in excess to the base.

The reaction product mixture is purified to remove by-products, such as the phosphonium oxide by-products that are generated through use of phosphonium-based ylides.

In one embodiment, the compound of formula (V) is (W). In this embodiment, W comprises groups $R^2$ and $R^{2'}$, which may be the same.

In one embodiment, compound (V) is (17).

(17)

In one aspect the present invention provides compounds of formula (V) with the proviso that the compound is not compound (17). In one embodiment, there is a further proviso that the compound of formula (V) is not compound (17a).

(17a)

Preferences

The following preferences may apply to all aspects of the invention as described above, or may relate to a single aspect. The preferences may be combined together in any combination.

$R^2$ and $R^{2'}$ $R^2$ is $CHR^{2A}$, and $R^{2A}$ is independently selected from H, R, $CO_2R$, COR, CHO, $CO_2H$, and halo.

In one embodiment, $R^{2A}$ is independently selected from H and R.

In one embodiment, $R^{2A}$ is independently selected from H, optionally substituted saturated $C_{1-6}$ alkyl and optionally substituted $C_{6-20}$ aryl.

In one embodiment, $R^{2A}$ is independently selected from H and unsubstituted saturated $C_{1-6}$ alkyl.

In one embodiment, $R^{2A}$ is independently selected from H and $CH_3$.

In one embodiment, $R^{2A}$ is independently selected from H.

Within a PBD compound, the group $R^2$ may have either configuration shown below:

(I)

-continued (II)

In one embodiment, the configuration is configuration (I).

The group $R^{2A}$ in compound (X) may be similarly located about the exo-double bond.

The preferences for $R^2$ are also applicable to $R^{2'}$.

In one embodiment, $R^2$ is the same as $R^{2'}$.

$R^6$ and $R^{6'}$ $R^6$ is independently selected from H, R, OH, OR, SH, SR, $NH_2$, NHR, NRR', $NO_2$, $Me_3Sn$— and Halo.

In one embodiment $R^6$ is independently selected from H, OH, OR, SH, $NH_2$, $NO_2$ and Halo.

In one embodiment $R^6$ is independently selected from H and Halo.

In one embodiment $R^6$ is independently selected from H.

The preferences for $R^6$ are also applicable to $R^{6'}$.

In one embodiment, $R^6$ is the same as $R^{6'}$.

$R^7$ and $R^{7'}$

In one embodiment, $R^7$ is independently OR.

In one embodiment, $R^7$ is independently OR, where R is optionally substituted saturated $C_{1-6}$ alkyl.

In one embodiment, $R^7$ is independently OMe.

In one embodiment, $R^7$ is independently $OCH_2Ph$.

The preferences for $R^7$ are also applicable to $R^{7'}$.

In one embodiment, $R^7$ is the same as $R^{7'}$.

In one embodiment, the compound is a dimer where the $R^7$ groups of each monomers form together a dimer bridge having the formula X—R"—X linking the monomers.

$R^8$ and $R^{8'}$

In one embodiment, $R^8$ is independently OR.

In one embodiment, $R^8$ is OR, where R is independently optionally substituted saturated $C_{1-6}$ alkyl.

In one embodiment, $R^8$ is independently OMe.

In one embodiment, $R^8$ is independently $OCH_2Ph$.

The preferences for $R^8$ are also applicable to $R^{8'}$.

In one embodiment, $R^8$ is the same as $R^{8'}$.

In one embodiment, the compound is a dimer where the $R^8$ groups of each monomers form together a dimer bridge having the formula X—R"—X linking the monomers.

$R^9$ and $R^{9'}$ $R^9$ is independently selected from H, R, OH, OR, SH, SR, $NH_2$, NHR, NRR', $NO_2$, $Me_3Sn$— and Halo.

In one embodiment, $R^9$ is H.

The preferences for $R^9$ are also applicable to $R^{9'}$.

In one embodiment, $R^9$ is the same as $R^{9'}$.

R"

R" is a $C_{3-12}$ alkylene group, which chain may be interrupted by one or more heteroatoms, e.g. O, S, N(H), and/or aromatic rings, e.g. benzene or pyridine.

In one embodiment, R" is a $C_{3-12}$ alkylene group.

In one embodiment, R" is selected from a $C_3$, $C_5$, $C_7$, $C_9$ and a $C_{11}$ alkylene group.

In one embodiment, R" is selected from a $C_3$, $C_5$ and a $C_7$ alkylene group.

In one embodiment, R" is selected from a $C_3$ and a $C_5$ alkylene group.

In one embodiment, R" is a $C_3$ alkylene group.

In one embodiment, R" is a $C_5$ alkylene group.

The alkylene groups listed above may be optionally interrupted by one or more heteroatoms, e.g. O, S, N(H), and/or aromatic rings, e.g. benzene or pyridine.

The alkylene groups listed above may be unsubstituted linear aliphatic alkylene groups.

X and X'

X is selected from O, S, or N(H). Preferably, X is O.

The preferences for X are also applicable to X'.

In one embodiment, X and X' are the same.

R and R'

R and R' are each independently selected from optionally substituted $C_{1-12}$ alkyl, $C_{3-20}$ heterocyclyl and $C_{5-20}$ aryl groups.

In one embodiment, R and R' are each optionally substituted $C_{1-12}$ alkyl.

In one embodiment, R and R' are each optionally substituted $C_{1-6}$ alkyl.

In one embodiment, R and R' are each optionally substituted saturated $C_{1-6}$ alkyl.

In one embodiment, R and R' are each optionally substituted saturated linear $C_{1-6}$ alkyl.

In one embodiment, R and R' are each selected from $CH_3$ and $CH_2CH_3$.

In one embodiment, R and R' are each $CH_3$.

In one embodiment, R and R' are each optionally substituted $C_{3-20}$ heterocyclyl.

In one embodiment, R and R' are each optionally substituted $C_{3-7}$ heterocyclyl.

In one embodiment, R and R' are each optionally substituted $C_{5-20}$ aryl groups.

In one embodiment, R and R' are each optionally substituted $C_{5-6}$ heteroarylaryl groups.

In one embodiment, R and R' are each optionally substituted $C_{610}$ carboaryl groups.

In one embodiment, R and R' are each optionally substituted phenyl.

In one embodiment, R and R' are each phenyl substituted with one or more groups selected from $C_{1-7}$ alkyl, halo, hydroxy, alkoxy, carboxy, ester, acyloxy, amino, amido, nitro, and sulfo.

In one embodiment, R and R' are each phenyl substituted with alkoxy.

In one embodiment, R and R' are the same.

In one embodiment, the preferred R and R' groups listed above may be unsubstituted.

Preferred Methods for the Synthesis of Compounds (M) and (O)

Compound (M) may be prepared from compound (X) and compound (N). Compound (O) may be prepared by the reaction of compound (X) with compound (N). Compound (M) may be prepared from compound (O).

Compound (M) may be prepared from compound (O). Preferably compound (M) is prepared from compound (O) via compound (T).

The preferences set out below for the reaction of compound (7) with (3) are generally applicable to the reaction of compound (X) with compound (N), unless otherwise stated to the contrary. The preferences for the preparation of compound (8) are likewise applicable to the preparation of compound (T) from compound (O).

Preferred Methods for the Synthesis of Compounds (A) and (B)

Compound (B) may be prepared by the reaction of compound (X) with compound (C).

The preferences set out below for the reaction of compound (7) with (3) are generally applicable to the reaction of compound (X) with compound (C), unless otherwise stated to the contrary.

In particular, it is preferred that the reaction is performed at elevated temperature, as described below.

Compound (A) may be prepared from compound (B). Preferably compound (A) is prepared from compound (B) via compound (S).

The preferences set out below for the preparation of SJG-136 from compound (7) via compound (8) are generally applicable to the preparation of compound (M) via compound (T), unless otherwise stated to the contrary.

SJG-136

In one aspect of the present invention there is provided a method of preparing SJG-136.

SJG-136 may be prepared from compound (8). Preferably compound (8) is reacted with a reducing agent. The reducing agent may be a borohydride salt. Preferably the reducing agent is lithium borohydride. Alternatively, the reducing agent is sodium borohydride.

The reaction may be driven to completion by the addition of excess reducing agent. The amount of reducing agent used may be 3, equivalents or more, 5 equivalents or more, or equivalents or more. The reducing agent may be added in one batch, or portionwise, over the course of the reaction.

The reaction is believed to proceed via the SEM carbinolamine compound (24) shown below:

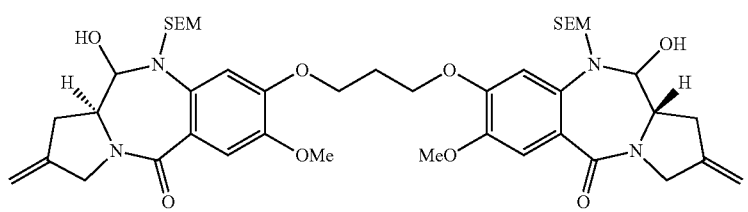

24

Small amounts of compound (24) may be recovered from the product mixture following chromatography. It is preferred that intermediate (24) is not isolated, and is treated with a SEM deprotecting reagent after the reduction step to yield the imine product (SJG-136). Preferably compound (24) is used within 24 hours of its preparation or isolation. Most preferably, intermediate (24) is used within 4 hours, within 2 hours or within 1 hour of its preparation or isolation.

Lithium borohydride is a stronger reducing agent than sodium borohydride and therefore allows the reduction reaction to proceed at a faster rate. As a consequence, the product may be isolated sooner before it is converted to an imine form which is highly susceptible to over reduction.

The product of the reduction step may be treated with a reagent capable of removing the nitrogen SEM protecting groups. Silica may be used. Alternatively, an organic acid may be used, such as citric acid or formic acid.

Compound (8)

The present invention provides compounds of formula (8) for use in a process for the preparation of SJG-136.

Compound (8) may be prepared from compound (7) by protecting the amide nitrogen atoms of compound (7) with SEM. Compound (7) may be treated with SEM-Cl in the presence of base. The base may be n-BuLi.

The reaction of compound (7) to form compound (8) is moisture sensitive. The highest yields are obtained in this reaction where fresh reagents are used, along with dry solvents and dry glassware. The yield is also increased when compound (7) is thoroughly dried.

Alternatively, compound (8) may be prepared from compound (18). Compound (18) may be treated with a methylene ylide. The ylide may be a phosphonium methylene ylide. The ylide may be generated from methyltriphenylphosphonium halide and a base, such as tert-butoxide salts. Preferably methyltriphenylphosphonium bromide is used in combination with potassium tert-butoxide.

Preferably the base used in the ylide forming step is freshly prepared. The methyltriphenylphosphonium halide is in excess to the base.

The reaction product mixture is purified to remove by-products, such as the phosphonium oxide by-products that are generated through use of phosphonium-based ylides.

Compound (7)

The present invention provides compounds of formula (7) for use in the preparation of SJG-136. Compound (7) may also find use in the preparation of compounds of formula (8).

Compound (7) may be prepared by reacting a compound of formula (3) with a compound of formula (6). Preferably the reaction is performed at elevated temperature. The reaction may be performed at 50° C. or more, 80° C. or more, 100° C. or more, or 110° C. or more. Preferably the reaction is performed at 110° C. or more. A suitable reaction solvent is DMSO.

A base may be used in the reaction. The base may be an organic base, such as DIPEA.

Reaction progression may be monitored by LC-MS.

The inventors have found that the reaction goes to completion after around 30 minutes at the preferred reaction temperature of 110° C. or more.

Cooper reports a coupling reaction using an alternative proline coupling partner and an analogue of compound (6) having a 5-carbon alkylene linker. The reaction mixture is heated for four hours at 100-120° C., far longer than the time required for the reaction of compounds (3) and (6). Thus, compounds (3) and (6) are more favourable coupling partners for they provide a proline-containing dimer structure in less time than previously reported.

As a final step, the product of the reaction may be further purified by trituration in an appropriate solvent. Acetonitrile may be used. This step is not essential however, as the inventors have found that the filtered and washed product may be used directly in the preparation of compound (8).

After the trituration, the product may be washed. Diethyl ether may be used.

Compound (7) should be thoroughly dried before use in the preparation of compound (8), as the formation of (8) is moisture sensitive.

Compound (6)

The present invention provides the use of compounds of formula (6) in the preparation of SJG-136. Compound (6) may also find use in the preparation of compounds of formula (7), and (8).

Compound (6) may be prepared from compound (5). Compound (5) may be reacted with triphosgene in the presence of base. The base may be pyridine or TEA. Preferably pyridine is used.

Compound (5) may be reacted with triphosgene at reflux.

The inventors have found that the reaction of (5) with triphosgene is optimally performed where compound (5) is used as a fine powder, owing to the relative insolubility of (5). Typically (5) may be prepared for the reaction by very fine grinding of the solids.

The reaction may be performed under reflux. Preferably the reflux reaction is performed for at least 2 hours, at least 4 hours, at least 6 hours, at least 12 hours or at least 24 hours.

This reaction is also described by Cooper on a related substrate having a 5-carbon alkylene linker.

Compound (5)

The present invention provides the use of compounds of formula (5) in the preparation of SJG-136. Compound (5) may also find use in the preparation of compounds of formula (6), (7), and (8).

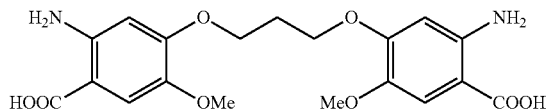

5

Compound (5) may be prepared from compound (4). Compound (5) may be prepared by reducing the nitro groups of compound (4).

Compound (4) may be reduced using hydrogen and a metal catalyst. The reaction may be performed under pressure using, for example, a Parr apparatus. The catalyst may be a palladium on carbon catalyst. The reaction may be performed at 40 psi or more (around 275 kPa or more), preferably about 45 psi (about 310 kPa).

Preferably compound (4) is treated with an aqueous base prior to hydrogenation. The reaction may be performed under aqueous conditions.

DMF may be used as a reaction solvent. However, care must be taken to remove this solvent from the final product, as the use of the product in the preparation of compound (6) involves the use of triphosgene, which will react with any contaminating DMF.

After hydrogen uptake in the reaction ceases, the catalyst may be removed by filtration. The filtrate may then be acidified, with aqueous HCl for example, and the resulting precipitate collected and dried in vaccuo. Phosphorus pentoxide may be as a drying reagent during.

Cooper has previously reported the hydrogenation of a compound analogous to compound (4) in ethanol and ethyl acetate (Cooper describes a compound having a 5-carbon alkylene linker). However, under these conditions the yield for the reaction was only 15%. In contrast, the methods of the present invention allow compound (5) to be obtained in quantitative yield from compound (4).

Compound (4)

The synthesis of compounds of formula (4) is described in the applicant's earlier application, WO 2006/111759. The preparation of compound (4) as described therein is specifically incorporated by reference herein. Example 1 in this earlier application is particularly relevant. WO 00/012508 also describes the preparation of compound (4) and is hereby incorporated by reference.

Briefly, compound (4), is derived from compound (9).

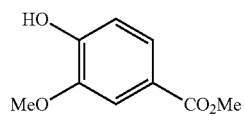

9

Compound (9) is dimerised to give compound (10).

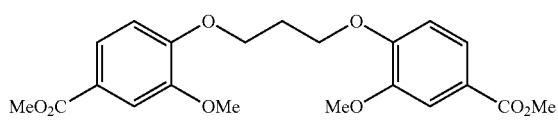

10

Nitration of the dimer (10) yields compound (11).

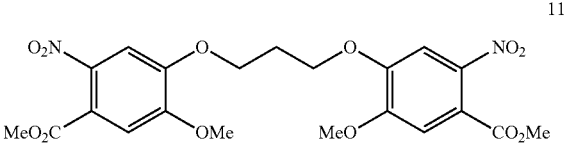 [SMILES: COC(=O)c1cc(OC)c(OCCCOc2cc([N+](=O)[O-])c(C(=O)OC)cc2OC)cc1[N+](=O)[O-]]

11

Compound (4) is obtained from (11) by hydrolysis of the methyl esters of compound (11).

In one embodiment of the invention, the preparation of any one of compounds (4), (8) and (13) to (18), and SJG-136 comprises any one of the steps described above, and disclosed in WO 2006/111759 and WO 00/012508.

Compound (3)

The present invention provides the use of compounds of formula (3) in the preparation of SJG-136. Compound (2) may also find use in the preparation of compounds (7) and (8).

Compound (3) may be used as a salt. A hydrochloride salt may be used.

Compound (3) may be prepared from compound (2). Compound (2) may be treated with a methylene ylide. Subsequently the amino-protecting group may be removed from the product of the initial reaction.

The ylide may be a phosphonium methylene ylide. The ylide may be generated from methyltriphenylphosphonium halide and a base, such as tert-butoxide salts. Preferably methyltriphenylphosphonium bromide is used in combination with potassium tert-butoxide.

Preferably the base used in the ylide forming step is freshly prepared. The methyltriphenylphosphonium halide is in excess to the base.

The reaction product mixture is purified to remove by-products, such as the phosphonium oxide by-products that are generated through use of phosphonium-based ylides.

The present inventors have found that the use of BuLi, as described by Narukawa et al., to generate the ylide was sensitive to the reaction conditions, and particularly to moisture and temperature. As an alternative, the present inventors have found that tert-butoxide salts are more managable, and advantageously provide greater yields. In particular potassium tert-butoxide may be used to generate the ylide.

The reaction proceeds via the Boc-protected acid (23) shown below:

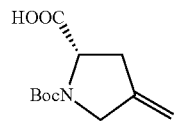

23

Compound (23) is treated with acid to remove the nitrogen protecting group. Where hydrochloric acid is used, the product of the reaction is the hydrochloric acid salt of compound (3).

Compound (23) may be obtained from commercial sources, if required (CAS number 84348-38-9).

Compound (3) is also described in WO 95/04718 which is incorporated by reference herein. Thus compound (3) may be prepared as described in Example 1 on page 19 and discussed on page 11.

Compound (2)

The present invention provides the use of compounds of formula (2) in the preparation of SJG-136. Compound (2) may also find use in the preparation of compounds (3), (7), and (8).

Compound (2) may be prepared from compound (1). Compound (2) may be prepared from compound (1) by oxidising the hydroxyl group of compound (1). Compound (1) may be oxidised with ruthenium oxide and periodate, preferably metaperiodate.

The oxidation of compound (1) with ruthenium oxide and periodate has been previously described in Narukawa Y., *Tetrahedron* 1997, 53, 539-556. However, under the conditions described, the reaction proceeds at a very slow rate. The inventors have found that increasing the equivalent amount of ruthenium oxide in the reaction increases the rate of reaction to an acceptable level. Thus, the amount of ruthenium oxide may be increased from 0.001 eq, as described in Narukawa, to 0.01 eq.

For the avoidance of doubt, the equivalency is expressed in relation to the molar amount of compound (1) used in the reaction.

The inventors have also found that increasing the temperature of the oxidation reaction increases the rate of reaction to an acceptable level. Thus, the reaction may be performed at temperature of 35° C. in comparison to the room temperature reaction described in Narukawa.

The product of the reaction may be purified by recrystallisation. However, the inventors have found that the crude product obtained after trituration is sufficiently pure to be used, for example, in the preparation of compound (3). In this way, the yield of product (65%) is comparable to that reported by Narukawa (also 65%).

The reaction may be monitored by LC-MS. Whilst UV detection methods are not generally helpful here given the relative invisibly of the product and starting material under UV light, the inventors have found that nevertheless the ES" trace produced by the MS is useful in determining reaction progression and reaction completion.

An alternative preparation of compound (2) is described in US 2007/185336. In particular, the oxidation of N-Boc-L-hydroxyproline to N-Boc-keto-L-proline as described on page 4 is specifically incorporated herein by reference.

Compound (1) is commercially available. Compound (2) may also be obtained from commercial sources.

Compound (17)

The present invention provides the use of compounds of formula (17) in the preparation of SJG-136. Compound (17) may also find use in the preparation of compound (8).

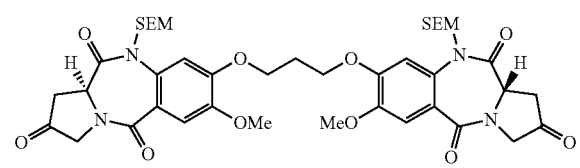

17

Compound (17) may be prepared by oxidising compound (16). Preferably compound (16) is oxidised with TEMPO.

The TEMPO-mediated oxidation reaction may be performed in the presence of bleach. In one embodiment the bleach is TCCA.

In an alternative embodiment the bleach is a hypochlorite salt, most preferably sodium hypochlorite. When hypochlorite salt is added to the reaction mixture, the temperature of the reaction mixture is held in the range 0 to 5° C.

Compound (16) may be oxidised under Swern-type oxidation conditions. Thus compound (16) may be treated with a mixture of oxalyl chloride and DMSO. The oxalyl chloride and DMSO may be combined prior to the addition of compound (16). Subsequently a base may be added to the reaction mixture. The base may be an organic base, and is most preferably TEA.

Compound (16)

The present invention provides the use of compounds of formula (16) in the preparation of SJG-136. Compound (16) may also find use in the preparation of compounds (8) and (17).

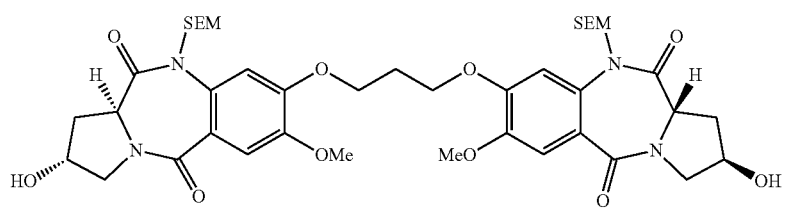

16

Compound (16) may be prepared by removing the hydroxy-protecting group of compound (15). Preferably compound (15) is deprotected with TBAF.

Compound (15)

The present invention provides the use of compounds of formula (15) in the preparation of SJG-136. Compound (15) may also find use in the preparation of compounds (8), (16), and (17).

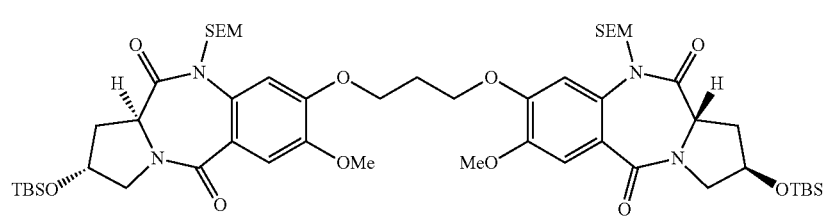

15

Compound (15) may be prepared by protecting the amide nitrogen atoms of compound (14) with SEM. Compound (14) may be treated with SEM-Cl in the presence of a base. The base may be n-BuLi. Compound (14) may be first treated with base. SEM-Cl may then be subsequently added. Alternatively, the base and SEM-Cl may be added to compound (14) at around the same time. The reaction may be performed in an ether solvent, preferably THF.

Compound (14)

The present invention provides the use of compounds of formula (14) in the preparation of SJG-136. Compound (14) may also find use in the preparation of compounds (8), (15), (16) and (17).

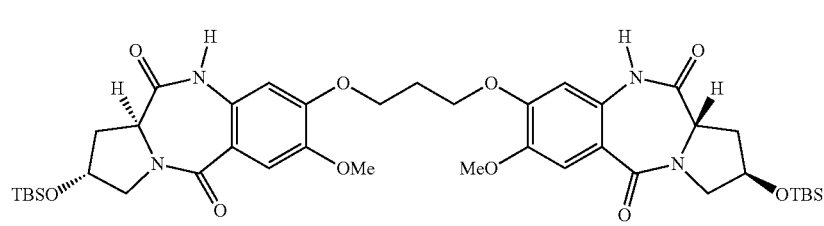

14

Compound (14) may be prepared from compound (13). The method of preparing compound (14) comprises the step of protecting the hydroxy groups of compound (13) with TBS. Preferably compound (13) is treated with TBS-Cl in the presence of base. Preferably the base is an organic base. The base may be imidazole.

Compound (13)

The present invention provides the use of compounds of formula (13) in the preparation of SJG-136. Compound (13) may also find use in the preparation of compounds (8), (14), (15), (16), and (17).

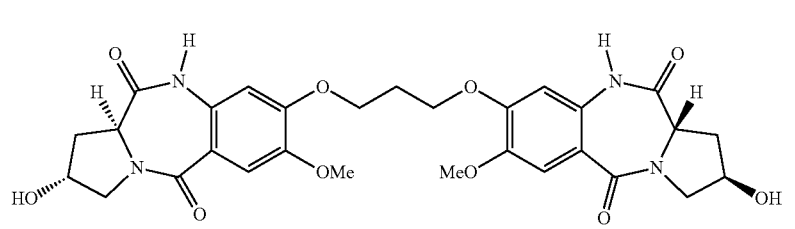

13

Compound (13) may be prepared from compound (12). The method of preparing compound (13) comprises the step of cyclising compound (12).

In a preferred embodiment of the invention, compound (12) may be treated with hydrogen in the presence of a catalyst. The catalyst may be a Pd/C catalyst. The reaction may be performed at greater than atmospheric pressure. Preferably the reaction is performed at 50 psi (~345 kPa). A Parr hydrogenation apparatus may be used.

Compound (12) may be first treated with hydrogen in the presence of the catalyst. Subsequently, hydrazine may be added. In one embodiment, the reaction mixture is purified to remove the catalyst before hydrazine is added to the reaction material. Typically, the reaction mixture is filtered to remove solid catalyst. A double filtration may be required to remove the majority of the catalyst material.

Hydrazine hydrate may be used in the reaction. The reaction may be performed at reflux. Ethanol may be used as a solvent for the reaction. It is preferred that the initial filtration of the reaction mixture is performed hot.

Alternatively, compound (12) may be treated with hydrazine in the presence of a Raney nickel catalyst. Preferably the reaction temperature is from 30 to 85° C., more preferably from 45 to 75° C., and most preferably 50 to 65° C.

Methanol may be used as a solvent in the reaction, in which case the reaction may be performed under reflux (~65° C.).

The inventors have established that the Raney nickel and hydrazine combination provides superior results compared to hydrogen with a Pd/C catalyst alone. Both methods provide improved yields compared to the sodium dithionite-mediated reaction described in WO 2006/111759 on an analogous nitro compound. A sodium dithionite-mediated reduction may find use in the present invention, though the methods described above are most preferred.

Previously, in WO 2004/04396 a reductive cyclisation was described using Pd/C with hydrogen followed by a HCl treatment step. This method may be adapted for the conversion of compound (12) to compound (13). However, this reaction may lead to racemisation of the product, and the methods described above are consequently preferred.

Compound (12)

The present invention provides the use of compounds of formula (12) in the preparation of SJG-136. Compound (12) may also find use in the preparation of compounds of formula (8), (13), (14), (15), (16), and (17).

Compound (12) may be prepared from compound (4).

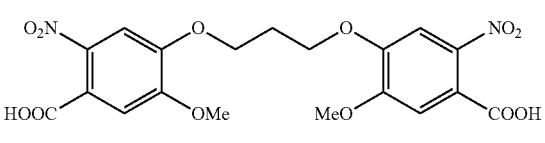

Compound (12) may be prepared by coupling compound (4) with methyl-4-hydroxypyrrolidine-2-carboxylate. Preferably the carboxylate is (2S,4R)-methyl-4-hydroxypyrrolidine-2-carboxylate. Preferably the hydrochloride salt of the carboxylate is used. The para-toluenesulfonate (p-TSOH) salt may also be used, though this is less preferred.

Compound (12) may be first treated with an activating agent to give the corresponding acid chloride compound. This compound may be isolated and stored for later use. The acid chloride may then be added to methyl-4-hydroxypyrrolidine-2-carboxylate.

The activating agent is added to generate the active ester form of compound (4). Preferably the activating agent is oxalyl chloride.

Preferably the coupling reaction is performed in the presence of base. The base may be an organic base. TEA may be used.

The inventors have established that compound (12) may be used advantageously in the preparation of benzodiazepine-containing compounds from compound (11). Compound (12) may be used as an intermediate for the synthesis of compound (14) and its analogues. In contrast with the route disclosed in WO 2006/111759, the benzodiazepine-containing compound of formula (14) may be accessed in two steps from compound (12) via compound (13). In contrast, WO 2006/111759 describes a preparation of a benzodiazepine-containing compound in five steps from compound (4).

SJG-720

SJG-720 finds use as an alternative to SJG-136 owing to its resistance to interconversion as described in WO 2005/042535. It is therefore suitable for formulation.

The preparation of SJG-720 from SJG-136 is described in detail in WO 2005/042535, which is incorporated by reference herein in its entirety. In particular, Example 1 is referred to.

The synthesis of SJG-720 involves the addition of a solution of the appropriate bisulfite salt to a solution of SJG-136, or their analogues, which is usually followed by a purification step.

Strategies for the Preparation of the Benzodiazepine Ring

The present invention provides improved methods for the preparation of compounds of formula (M) and in particular SJG-136. The invention also allows the preparation of a ben-

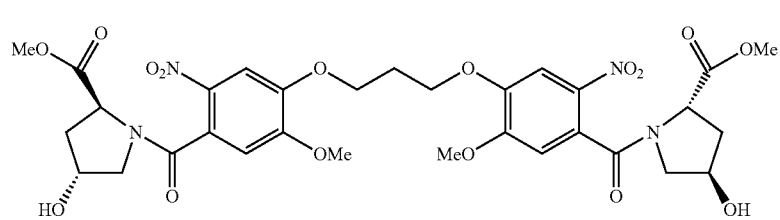

zodiazepine ring in fewer steps compared to those methods described previously in the art.

As described herein, there are two approaches to the formation of the benzodiazepine ring (the B-ring) in a PBD compound. In the convergent approach described herein, the B-ring may be formed at the same time as the A- and C-rings are linked together. In the linear approach descried herein, the B-ring may be formed after the A- and C-rings are linked together.

Both routes to the formation of the B-ring are improvements on the methods described in the art.

B-Ring Formation after A- and C-Rings are Linked

WO 2006/111759 describes the preparation of a benzodiazepine ring in a dimer structure. The initial preparation of the ring starts from compound (4) which is coupled with compound (18) to give compound (19).

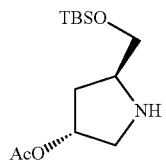
18

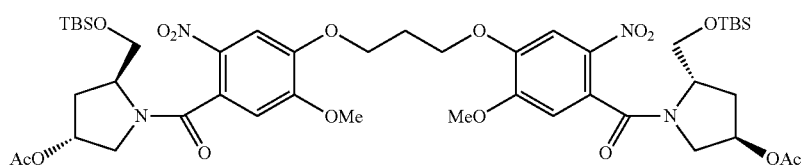
19

The nitro group of compound (19) is then reduced to give compound (20).

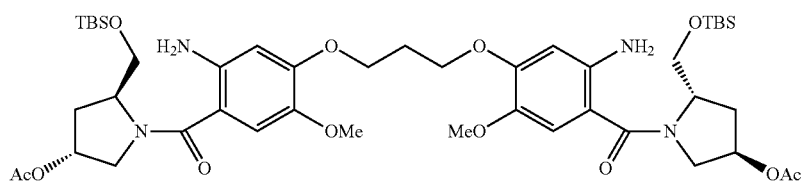
20

Compound (20) is then treated to remove the silyl protecting groups, to give compound (21).

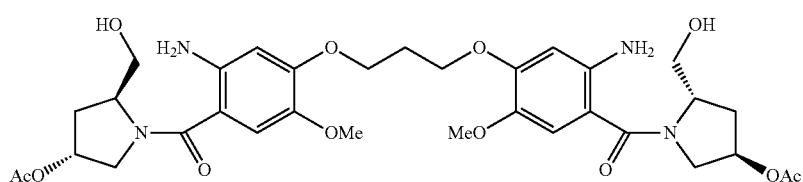
21

Compound (21) is then converted to the benzodiazepine dimer compound of formula (22) by treatment with TEMPO and BAIB.

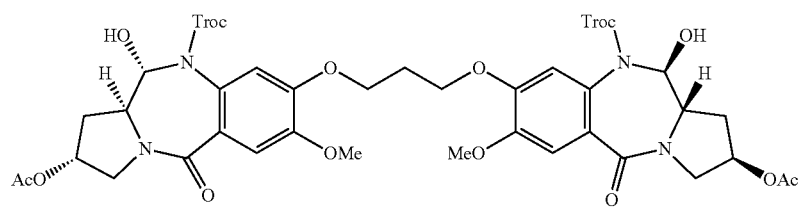

Compound (22) is described for use in the preparation of PBD compounds having a range of substituents at the C2 position.

The inventors have established that the a dimer comprising a pair of benzodiazepine rings may be prepared from compound (4) in greater yield and in fewer steps compared to the method described in WO 2006/111759.

Thus, the preferred linear method described herein allows the benzodiazepine-containing compound of formula (13) to be prepared from compound (4) in two steps and 79% overall yield.

In contrast, the first benzodiazepine-containing compound described in WO 2006/111759 is compound (22) which is obtained from compound (4) in five steps and 15% overall yield.

B-Ring Formation at the Same as the A- and C-Rings are Linked Together

The present invention provides a method for the preparation of a B-ring in a PBD compound at the same time as the A- and C-rings are linked together. The yield for this single step is 50% as reported herein. Combining these steps in one procedure reduces the complexity of the overall synthesis of compounds (M) and (O), and reduces the overall time needed to prepare these PBD compounds.

Convergent Approach

As described above in relation to compounds (M), (N), (O) and (X) (and in particular compounds (A), (B) and (C)), the present invention provides methods for the preparation of PBD compounds, and in particular SJG-136, using a convergent approach to the PBD core and the C-ring C2 substituent. This approach may provide the target PBD compound in less time and in fewer steps compared to other routes.

Alternatively, SJG-136 may be prepared using a linear approach to the PBD core and the C-ring C2 substituent, as described in more detail below.

The convergent and linear approaches may be used to prepare compound (M). The preferences set out here and below are generally applicable to the preparation of compound (M), unless otherwise stated to the contrary.

Linear Approach

SJG-136 may be prepared using a linear approach to the PBD core and the C-ring C2 substituent.

The key strategy in the linear approach is the formation of the exo-double bond at the C2 position after the A- and C-rings have been linked, and either before or after the B-ring has been formed. The present invention provides a method where the B-ring is formed prior to the introduction of the required C2 functionality. In another approach, such as described in Gregson et al. (J. Med. Chem. 2001, 44, 1161-1174), the substituent required at the C2 position may be introduced after the A- and C-rings are connected. The B-ring is then formed at a later stage in the synthesis.

The advantage of the linear approach is that is allows an advanced reactive substrate to be prepared, such as compound (18), which can be converted into a range of different C2 functionalised products e.g. by appropriate choice of Wittig coupling partner.

The convergent approach, in contrast, requires the preparation of a different proline-based residue for each C2 functionalised product that is to be prepared. Consequently, the convergent approach is best suited to a targeted preparation, whilst the linear approach allows a more expansive structural area to be explored.

Preferred Synthesis of SJG-136

In one aspect of the invention there is provided a process of preparing SJG-136 comprising one or more of the steps described above. In a preferred embodiment, the preparation of SJG-136 comprises two or more of the steps described above.

SJG-136 may be prepared in a multi-step synthesis. The intermediates in the synthesis may be one or more of the compounds discussed above.

In a preferred process of preparing SJG-136, the process comprises one or more of the following methods:

(i) the synthesis of compound (8) by protecting the amide nitrogen atoms of compound (7) with SEM as described herein;
(ii) the synthesis of compound (7) by reacting compound (6) with compound (3) as described herein;
(iii) the synthesis of compound (3) by reacting compound (2) as described herein;
(iv) the synthesis of compound (2) oxidising compound (1) as described herein;
(v) the synthesis of compound (6) by reacting compound (5) as described herein;
(vi) the synthesis of compound (5) reducing the nitro groups of compound (4) as described herein;
(vii) the synthesis of compound (8) by reacting compound (17) as described herein;
(viii) the synthesis of compound (17) by oxidising compound (16) as described herein;
(ix) the synthesis of compound (16) by removing the hydroxy-protecting groups of compound (15) as described herein;
(x) the synthesis of compound (15) by protecting the amide nitrogen atoms of compound (14) with SEM as described herein;
(xi) the synthesis of compound (14) by protecting the hydroxy groups of compound (13) with TBS as described herein;
(xii) the synthesis of compound (13) by cyclising compound (12) as described herein;

(xiii) the synthesis of compound (12) by coupling compound (4) with methyl-4-hydroxypyrrolidine-2-carboxylate as described herein.

(xiii) the synthesis of SJG-136 by reacting compound (8) as described herein.

In one embodiment, steps (i) to (vi), and (xiii) may be used in combination to prepare SJG-136. This combination may be referred to as the convergent approach to SJG-136.

In one embodiment, steps (vii) to (xiii) may be used in combination to prepare SJG-136. This combination may be referred to as the linear approach to SJG-136.

When steps (i) to (vi) and (xiii) are used in combination in the preparation of SJG-136, the overall yield from compound (4) is significantly increased compared to the yields reported in the art. By the convergent approach, the present invention provides SJG-136 in 5 steps from compound (4) and 23.5% overall yield. In comparison, WO 00/12508 describes the preparation of SJG-136 in 6 steps from compound (4) and 6.6% overall yield.

When steps (vii) to (xiii) are used in combination in the preparation of SJG-136, the overall yield from compound (4) is significantly increased compared to the yields reported in the art. By a linear approach, the present invention provides SJG-136 in 8 steps from compound (4) and 12.2% overall yield. In comparison, Gregson et al. (*J. Med. Chem.* 2001, 44, 1161-1174) describes the preparation of SJG-136 in 8 steps from compound (4) and 8.6% overall yield.

Preferred Synthesis of SJG-720

In one aspect of the invention there is provided a process of preparing SJG-720 comprising one or more of the steps described above.

SJG-720 may be prepared in a multi-step synthesis. The intermediates in the synthesis may be one or more of the compounds discussed above.

In a preferred process of preparing SJG-720, the process comprises one or more of the steps (i) to (xiii) described above and step (xiv):

(xiv) the synthesis of SJG-720 by treating SJG-136 with a bisulfite salt as described herein.

In one embodiment, steps (i) to (vi), (xiii) and (xiv) may be used in combination to prepare SJG-720.

In one embodiment, steps (vii) to (xiv) may be used in combination to prepare SJG-720.

As described above, SJG-136 may be prepared in fewer steps and in greater yield compared to those methods described in the art. SJG-720, which is prepared directly from SJG-136, may be similarly obtained in fewer steps and in greater yield compared to those methods described in the art.

Definitions

The phrase "optionally substituted" as used herein, pertains to a parent group which may be unsubstituted or which may be substituted.

Unless otherwise specified, the term "substituted" as used herein, pertains to a parent group which bears one or more substituents. The term "substituent" is used herein in the conventional sense and refers to a chemical moiety which is covalently attached to, or if appropriate, fused to, a parent group. A wide variety of substituents are well known, and methods for their formation and introduction into a variety of parent groups are also well known.

Examples of substituents are described in more detail below. $C_{1-7}$ alkyl: The term "$C_{1-7}$ alkyl" as used herein, pertains to a monovalent moiety obtained by removing a hydrogen atom from a carbon atom of a hydrocarbon compound having from 1 to 7 carbon atoms, which may be aliphatic or alicyclic, and which may be saturated or unsaturated (e.g. partially unsaturated, fully unsaturated). Thus, the term "alkyl" includes the sub-classes alkenyl, alkynyl, cycloalkyl, etc., discussed below.

Examples of saturated alkyl groups include, but are not limited to, methyl ($C_1$), ethyl ($C_2$), propyl ($C_3$), butyl ($C_4$), pentyl ($C_5$), hexyl ($C_6$) and heptyl ($C_7$).

Examples of saturated linear alkyl groups include, but are not limited to, methyl ($C_1$), ethyl ($C_2$), n-propyl ($C_3$), n-butyl ($C_4$), n-pentyl (amyl) ($C_5$), n-hexyl ($C_6$) and n-heptyl ($C_7$).

Examples of saturated branched alkyl groups include iso-propyl ($C_3$), iso-butyl ($C_4$), sec-butyl ($C_4$), tert-butyl ($C_4$), iso-pentyl ($C_5$), and neo-pentyl ($C_5$).

$C_{2-7}$ Alkenyl: The term "$C_{2-7}$ alkenyl" as used herein, pertains to an alkyl group having one or more carbon-carbon double bonds.

Examples of unsaturated alkenyl groups include, but are not limited to, ethenyl (vinyl, —CH=CH$_2$), 1-propenyl (—CH=CH—CH$_3$), 2-propenyl (allyl, —CH—CH=CH$_2$), isopropenyl (1-methylvinyl, —C(CH$_3$)=CH$_2$), butenyl ($C_4$), pentenyl ($C_5$), and hexenyl ($C_6$).

$C_{2-7}$ alkynyl: The term "$C_{2-7}$ alkynyl" as used herein, pertains to an alkyl group having one or more carbon-carbon triple bonds.

Examples of unsaturated alkynyl groups include, but are not limited to, ethynyl (ethinyl, —C≡CH) and 2-propynyl (propargyl, —CH$_2$—C≡CH).

$C_{3-7}$ cycloalkyl: The term "$C_{3-7}$ cycloalkyl" as used herein, pertains to an alkyl group which is also a cyclyl group; that is, a monovalent moiety obtained by removing a hydrogen atom from an alicyclic ring atom of a cyclic hydrocarbon (carbocyclic) compound, which moiety has from 3 to 7 carbon atoms, including from 3 to 7 ring atoms.

Examples of cycloalkyl groups include, but are not limited to, those derived from:

saturated monocyclic hydrocarbon compounds:
cyclopropane ($C_3$), cyclobutane ($C_4$), cyclopentane ($C_5$), cyclohexane ($C_6$), cycloheptane ($C_7$), methylcyclopropane ($C_4$), dimethylcyclopropane ($C_5$), methylcyclobutane ($C_5$), dimethylcyclobutane ($C_6$), methylcyclopentane ($C_6$), dimethylcyclopentane ($C_7$) and methylcyclohexane ($C_7$);

unsaturated monocyclic hydrocarbon compounds:
cyclopropene ($C_3$), cyclobutene ($C_4$), cyclopentene ($C_5$), cyclohexene ($C_6$), methylcyclopropene ($C_4$), dimethylcyclopropene ($C_5$), methylcyclobutene ($C_5$), dimethylcyclobutene ($C_6$), methylcyclopentene ($C_6$), dimethylcyclopentene ($C_7$) and methylcyclohexene ($C_7$); and saturated polycyclic hydrocarbon compounds:
norcarane ($C_7$), norpinane ($C_7$), norbornane ($C_7$).

$C_{3-20}$ heterocyclyl: The term "$C_{3-20}$ heterocyclyl" as used herein, pertains to a monovalent moiety obtained by removing a hydrogen atom from a ring atom of a heterocyclic compound, which moiety has from 3 to 20 ring atoms, of which from 1 to 10 are ring heteroatoms. Preferably, each ring has from 3 to 7 ring atoms, of which from 1 to 4 are ring heteroatoms.

In this context, the prefixes (e.g. $C_{3-20}$, $C_{3-7}$, $C_{5-6}$, etc.) denote the number of ring atoms, or range of number of ring atoms, whether carbon atoms or heteroatoms. For example, the term "$C_{5-6}$heterocyclyl", as used herein, pertains to a heterocyclyl group having 5 or 6 ring atoms.

Examples of monocyclic heterocyclyl groups include, but are not limited to, those derived from:

$N_1$: aziridine ($C_3$), azetidine ($C_4$), pyrrolidine (tetrahydropyrrole) ($C_5$), pyrroline (e.g., 3-pyrroline, 2,5-dihydropyrrole) ($C_5$), 2H-pyrrole or 3H-pyrrole (isopyrrole, isoazole) ($C_5$), piperidine ($C_6$), dihydropyridine ($C_6$), tetrahydropyridine ($C_6$), azepine ($C_7$);

$O_1$: oxirane ($C_3$), oxetane ($C_4$), oxolane (tetrahydrofuran) ($C_5$), oxole (dihydrofuran) ($C_5$), oxane (tetrahydropyran) ($C_6$), dihydropyran ($C_6$), pyran ($C_6$), oxepin ($C_7$);

$S_1$: thiirane ($C_3$), thietane ($C_4$), thiolane (tetrahydrothiophene) ($C_5$), thiane (tetrahydrothiopyran) ($C_6$), thiepane ($C_7$);

$O_2$: dioxolane ($C_5$), dioxane ($C_6$), and dioxepane ($C_7$);

$O_3$: trioxane ($C_6$);

$N_2$: imidazolidine ($C_5$), pyrazolidine (diazolidine) ($C_5$), imidazoline ($C_5$), pyrazoline (dihydropyrazole) ($C_5$), piperazine ($C_6$);

$N_1O_1$: tetrahydrooxazole ($C_5$), dihydrooxazole ($C_5$), tetrahydroisoxazole ($C_5$), dihydroisoxazole ($C_5$), morpholine ($C_6$), tetrahydrooxazine ($C_6$), dihydrooxazine ($C_6$), oxazine ($C_6$);

$N_1S_1$: thiazoline ($C_5$), thiazolidine ($C_5$), thiomorpholine ($C_6$);

$N_2O_1$: oxadiazine ($C_6$);

$O_1S_1$: oxathiole ($C_5$) and oxathiane (thioxane) ($C_6$); and, $N_1O_1S_1$: oxathiazine ($C_6$).

Examples of substituted monocyclic heterocyclyl groups include those derived from saccharides, in cyclic form, for example, furanoses ($C_5$), such as arabinofuranose, lyxofuranose, ribofuranose, and xylofuranse, and pyranoses ($C_6$), such as allopyranose, altropyranose, glucopyranose, mannopyranose, gulopyranose, idopyranose, galactopyranose, and talopyranose.

$C_{5-20}$ aryl: The term "$C_{5-20}$ aryl", as used herein, pertains to a monovalent moiety obtained by removing a hydrogen atom from an aromatic ring atom of an aromatic compound, which moiety has from 3 to 20 ring atoms. Preferably, each ring has from 5 to 7 ring atoms.

In this context, the prefixes (e.g. $C_{3-20}$, $C_{5-7}$, $C_{5-6}$, etc.) denote the number of ring atoms, or range of number of ring atoms, whether carbon atoms or heteroatoms. For example, the term "$C_{5-6}$ aryl" as used herein, pertains to an aryl group having 5 or 6 ring atoms.

The ring atoms may be all carbon atoms, as in "carboaryl groups".

Examples of carboaryl groups include, but are not limited to, those derived from benzene (i.e. phenyl) ($C_6$), naphthalene ($C_{10}$), azulene ($C_{10}$), anthracene ($C_{14}$), phenanthrene ($C_{14}$), naphthacene ($C_{18}$), and pyrene ($C_{16}$).

Examples of aryl groups which comprise fused rings, at least one of which is an aromatic ring, include, but are not limited to, groups derived from indane (e.g. 2,3-dihydro-1H-indene) ($C_9$), indene ($C_9$), isoindene ($C_9$), tetraline (1,2,3,4-tetrahydronaphthalene) ($C_{10}$), acenaphthene ($C_{12}$), fluorene ($C_{13}$), phenalene ($C_{13}$), acephenanthrene ($C_{15}$), and aceanthrene ($C_{16}$).

Alternatively, the ring atoms may include one or more heteroatoms, as in "heteroaryl groups". Examples of monocyclic heteroaryl groups include, but are not limited to, those derived from:

$N_1$: pyrrole (azole) ($C_5$), pyridine (azine) ($C_6$);

$O_1$: furan (oxole) ($C_5$);

$S_1$: thiophene (thiole) ($C_5$);

$N_1O_1$: oxazole ($C_5$), isoxazole ($C_5$), isoxazine ($C_6$);

$N_2O_1$: oxadiazole (furazan) ($C_5$);

$N_3O_1$: oxatriazole ($C_5$);

$N_1S_1$: thiazole ($C_5$), isothiazole ($C_5$);

$N_2$: imidazole (1,3-diazole) ($C_5$), pyrazole (1,2-diazole) ($C_5$), pyridazine (1,2-diazine) ($C_6$), pyrimidine (1,3-diazine) ($C_6$) (e.g., cytosine, thymine, uracil), pyrazine (1,4-diazine) ($C_6$);

$N_3$: triazole ($C_5$), triazine ($C_6$); and, $N_4$: tetrazole ($C_5$).

Examples of heteroaryl which comprise fused rings, include, but are not limited to:

$C_9$ (with 2 fused rings) derived from benzofuran ($O_1$), isobenzofuran ($O_1$), indole ($N_1$), isoindole ($N_1$), indolizine ($N_1$), indoline ($N_1$), isoindoline ($N_1$), purine ($N_4$) (e.g., adenine, guanine), benzimidazole ($N_2$), indazole ($N_2$), benzoxazole ($N_1O_1$), benzisoxazole ($N_1O_1$), benzodioxole ($O_2$), benzofurazan ($N_2O_1$), benzotriazole ($N_3$), benzothiofuran ($S_1$), benzothiazole ($N_1S_1$), benzothiadiazole ($N_2S$);

$C_{10}$ (with 2 fused rings) derived from chromene ($O_1$), isochromene ($O_1$), chroman ($O_1$), isochroman ($O_1$), benzodioxan ($O_2$), quinoline ($N_1$), isoquinoline ($N_1$), quinolizine ($N_1$), benzoxazine ($N_1O_1$), benzodiazine ($N_2$), pyridopyridine ($N_2$), quinoxaline ($N_2$), quinazoline ($N_2$), cinnoline ($N_2$), phthalazine ($N_2$), naphthyridine ($N_2$), pteridine ($N_4$);

$C_{11}$ (with 2 fused rings) derived from benzodiazepine ($N_2$);

$C_{13}$ (with 3 fused rings) derived from carbazole ($N_1$), dibenzofuran ($O_1$), dibenzothiophene ($S_1$), carboline ($N_2$), perimidine ($N_2$), pyridoindole ($N_2$); and, $C_{14}$ (with 3 fused rings) derived from acridine ($N_1$), xanthene ($O_1$), thioxanthene ($S_1$), oxanthrene ($O_2$), phenoxathiin ($O_1S_1$), phenazine ($N_2$), phenoxazine ($N_1O_1$), phenothiazine ($N_1S_1$), thianthrene ($S_2$), phenanthridine ($N_1$), phenanthroline ($N_2$), phenazine ($N_2$).

The above groups, whether alone or part of another substituent, may themselves optionally be substituted with one or more groups selected from themselves and the additional substituents listed below.

Halo: —F, —Cl, —Br, and —I.

Hydroxy: —OH.

Ether: —OR, wherein R is an ether substituent, for example, a $C_{1-7}$ alkyl group (also referred to as a $C_{1-7}$ alkoxy group, discussed below), a $C_{3-20}$ heterocyclyl group (also referred to as a $C_{3-20}$ heterocyclyloxy group), or a $C_{5-20}$ aryl group (also referred to as a $C_{5-20}$ aryloxy group), preferably a $C_{1-7}$alkyl group.

Alkoxy: —OR, wherein R is an alkyl group, for example, a $C_{1-7}$ alkyl group. Examples of $C_{1-7}$ alkoxy groups include, but are not limited to, —OMe (methoxy), —OEt (ethoxy), —O(nPr) (n-propoxy), —O(iPr) (isopropoxy), —O(nBu) (n-butoxy), —O(sBu) (sec-butoxy), —O(iBu) (isobutoxy), and —O(tBu) (tert-butoxy).

Acetal: —CH(OR$^1$)(OR$^2$), wherein R$^1$ and R$^2$ are independently acetal substituents, for example, a $C_{1-7}$ alkyl group, a $C_{3-20}$ heterocyclyl group, or a $C_{5-20}$ aryl group, preferably a $C_{1-7}$ alkyl group, or, in the case of a "cyclic" acetal group, R$^1$ and R$^2$, taken together with the two oxygen atoms to which they are attached, and the carbon atoms to which they are attached, form a heterocyclic ring having from 4 to 8 ring atoms. Examples of acetal groups include, but are not limited to, —CH(OMe)$_2$, —CH(OEt)$_2$, and —CH(OMe)(OEt).

Hemiacetal: —CH(OH)(OR$^1$), wherein R$^1$ is a hemiacetal substituent, for example, a $C_{1-7}$ alkyl group, a $C_{3-20}$ heterocyclyl group, or a $C_{5-20}$ aryl group, preferably a $C_{1-7}$ alkyl group. Examples of hemiacetal groups include, but are not limited to, —CH(OH)(OMe) and —CH(OH)(OEt).

Ketal: —CR(OR$^1$)(OR$^2$), where R$^1$ and R$^2$ are as defined for acetals, and R is a ketal substituent other than hydrogen, for example, a $C_{1-7}$ alkyl group, a $C_{3-20}$ heterocyclyl group, or a $C_{5-20}$ aryl group, preferably a $C_{1-7}$ alkyl group. Examples ketal groups include, but are not limited to, —C(Me)(OMe)$_2$, —C(Me)(OEt)$_2$, —C(Me)(OMe)(OEt), —C(Et)(OMe)$_2$, —C(Et)(OEt)$_2$, and —C(Et)(OMe)(OEt).

Hemiketal: —CR(OH)(OR$^1$), where R$^1$ is as defined for hemiacetals, and R is a hemiketal substituent other than hydrogen, for example, a $C_{1-7}$ alkyl group, a $C_{3-20}$ heterocyclyl group, or a $C_{5-20}$ aryl group, preferably a $C_{1-7}$ alkyl group.

Examples of hemiacetal groups include, but are not limited to, —C(Me)(OH)(OMe), —C(Et)(OH)(OMe), —C(Me)(OH)(OEt), and —C(Et)(OH)(OEt).

Oxo (keto, -one): =O.

Thione (thioketone): =S.

Imino (imine): =NR, wherein R is an imino substituent, for example, hydrogen, $C_{1-7}$ alkyl group, a $C_{3-20}$ heterocyclyl group, or a $C_{5-20}$ aryl group, preferably hydrogen or a $C_{1-7}$ alkyl group. Examples of ester groups include, but are not limited to, =NH, =NMe, =NEt, and =NPh.

Formyl (carbaldehyde, carboxaldehyde): —C(=O)H.

Acyl (keto): —C(=O)R, wherein R is an acyl substituent, for example, a $C_{1-7}$ alkyl group (also referred to as $C_{1-7}$ alkylacyl or $C_{1-7}$ alkanoyl), a $C_{3-20}$ heterocyclyl group (also referred to as $C_{3-20}$ heterocyclylacyl), or a $C_{5-20}$ aryl group (also referred to as $C_{5-20}$ arylacyl), preferably a $C_{1-7}$ alkyl group. Examples of acyl groups include, but are not limited to, —C(=O)CH$_3$ (acetyl), —C(=O)CH$_2$CH$_3$ (propionyl), —C(=O)C(CH$_3$)$_3$ (t-butyryl), and —C(=O)Ph (benzoyl, phenone).

Carboxy (carboxylic acid): —C(=O)OH.

Thiocarboxy (thiocarboxylic acid): —C(=S)SH.

Thiolocarboxy (thiolocarboxylic acid): —C(=O)SH.

Thionocarboxy (thionocarboxylic acid): —C(=S)OH.

Imidic acid: —C(=NH)OH.

Hydroxamic acid: —C(=NOH)OH.

Ester (carboxylate, carboxylic acid ester, oxycarbonyl): —C(=O)OR, wherein R is an ester substituent, for example, a $C_{1-7}$ alkyl group, a $C_{3-20}$ heterocyclyl group, or a $C_{5-20}$ aryl group, preferably a $O_{1-7}$ alkyl group. Examples of ester groups include, but are not limited to, —C(=O)OCH$_3$, —C(=O)OCH$_2$CH$_3$, —C(=O)OC(CH$_3$)$_3$, and —C(=O)OPh.

Acyloxy (reverse ester): —OC(=O)R, wherein R is an acyloxy substituent, for example, a $C_{1-7}$ alkyl group, a $C_{3-20}$ heterocyclyl group, or a $C_{5-20}$ aryl group, preferably a $C_{1-7}$ alkyl group. Examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, and —OC(=O)CH$_2$Ph.

Oxycarboyloxy: —OC(=O)OR, wherein R is an ester substituent, for example, a $C_{1-7}$ alkyl group, a $C_{3-20}$ heterocyclyl group, or a $C_{5-20}$ aryl group, preferably a $C_{1-7}$ alkyl group. Examples of ester groups include, but are not limited to, —OC(=O)OCH$_3$, —OC(=O)OCH$_2$CH$_3$, —OC(=O)OC(CH$_3$)$_3$, and —OC(=O)OPh.

Amino: —NR$^1$R$^2$, wherein R$^1$ and R$^2$ are independently amino substituents, for example, hydrogen, a $C_{1-7}$ alkyl group (also referred to as $C_{1-7}$ alkylamino or di-$C_{1-7}$ alkylamino), a $C_{3-20}$ heterocyclyl group, or a $C_{5-20}$ aryl group, preferably H or a $C_{1-7}$ alkyl group, or, in the case of a "cyclic" amino group, R$^1$ and R$^2$, taken together with the nitrogen atom to which they are attached, form a heterocyclic ring having from 4 to 8 ring atoms. Amino groups may be primary (—NH$_2$), secondary (—NHR$^1$), or tertiary (—NHR$^1$R$^2$), and in cationic form, may be quaternary (—$^+$NR$^1$R$^2$R$^3$). Examples of amino groups include, but are not limited to, —NH$_2$, —NHCH$_3$, —NHC(CH$_3$)$_2$, —N(CH$_3$)$_2$, —N(CH$_2$CH$_3$)$_2$, and —NHPh. Examples of cyclic amino groups include, but are not limited to, aziridino, azetidino, pyrrolidino, piperidino, piperazino, morpholino, and thiomorpholino.

Amido (carbamoyl, carbamyl, aminocarbonyl, carboxamide): —C(=O)NR$^1$R$^2$, wherein R$^1$ and R$^2$ are independently amino substituents, as defined for amino groups. Examples of amido groups include, but are not limited to, —C(=O)NH$_2$, —C(=O)NHCH$_3$, —C(=O)N(CH$_3$)$_2$, —C(=O)NHCH$_2$CH$_3$, and —C(=O)N(CH$_2$CH$_3$)$_2$, as well as amido groups in which R$^1$ and R$^2$, together with the nitrogen atom to which they are attached, form a heterocyclic structure as in, for example, piperidinocarbonyl, morpholinocarbonyl, thiomorpholinocarbonyl, and piperazinocarbonyl.

Thioamido (thiocarbamyl): —C(=S)NR$^1$R$^2$, wherein R$^1$ and R$^2$ are independently amino substituents, as defined for amino groups. Examples of amido groups include, but are not limited to, —C(=S)NH$_2$, —C(=S)NHCH$_3$, —C(=S)N(CH$_3$)$_2$, and —C(=S)NHCH$_2$CH$_3$.

Acylamido (acylamino): —NR$^1$C(=O)R$^2$, wherein R$^1$ is an amide substituent, for example, hydrogen, a $C_{1-7}$ alkyl group, a $C_{3-20}$ heterocyclyl group, or a $O_{5-20}$ aryl group, preferably hydrogen or a $C_{1-7}$ alkyl group, and R$^2$ is an acyl substituent, for example, a $C_{1-7}$ alkyl group, a $C_{3-20}$ heterocyclyl group, or a $C_{5-20}$ aryl group, preferably hydrogen or a $C_{1-7}$ alkyl group. Examples of acylamide groups include, but are not limited to, —NHC(=O)CH$_3$, —NHC(=O)CH$_2$CH$_3$, and —NHC(=O)Ph. R$^1$ and R$^2$ may together form a cyclic structure, as in, for example, succinimidyl, maleimidyl, and phthalimidyl:

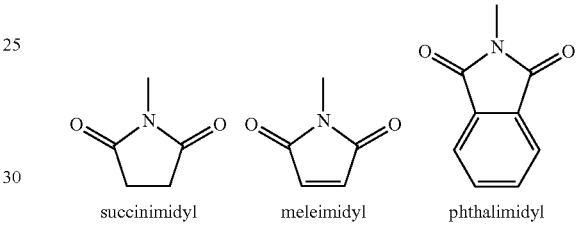

succinimidyl    meleimidyl    phthalimidyl

Aminocarbonyloxy: —OC(=O)NR$^1$R$^2$, wherein R$^1$ and R$^2$ are independently amino substituents, as defined for amino groups. Examples of aminocarbonyloxy groups include, but are not limited to, —OC(=O)NH$_2$, —OC(=O)NHMe, —OC(=O)NMe$_2$, and —OC(=O)NEt$_2$.

Ureido: —N(R$^1$)CONR$^2$R$^3$ wherein R$^2$ and R$^3$ are independently amino substituents, as defined for amino groups, and R$^1$ is a ureido substituent, for example, hydrogen, a $C_{1-7}$ alkyl group, a $C_{3-20}$ heterocyclyl group, or a $C_{5-20}$ aryl group, preferably hydrogen or a $C_{1-7}$ alkyl group. Examples of ureido groups include, but are not limited to, —NHCONH$_2$, —NHCONHMe, —NHCONHEt, —NHCONMe$_2$, —NHCONEt$_2$, —NMeCONH$_2$, —NMeCONHMe, —NMeCONHEt, —NMeCONMe$_2$, and —NMeCONEt$_2$.

Guanidino: —NH—C(=NH)NH$_2$.

Tetrazolyl: a five membered aromatic ring having four nitrogen atoms and one carbon atom,

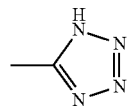

Imino: =NR, wherein R is an imino substituent, for example, for example, hydrogen, a $C_{1-7}$ alkyl group, a $C_{3-20}$ heterocyclyl group, or a $C_{5-20}$ aryl group, preferably H or a $C_{1-7}$ alkyl group. Examples of imino groups include, but are not limited to, =NH, =NMe, and =NEt.

Amidine (amidino): —C(=NR)NR$_2$, wherein each R is an amidine substituent, for example, hydrogen, a $C_{1-7}$ alkyl group, a $C_{3-20}$ heterocyclyl group, or a $C_{5-20}$ aryl group, preferably H or a $C_{1-7}$ alkyl group. Examples of amidine groups include, but are not limited to, —C(=NH)NH$_2$, —C(=NH)NMe$_2$, and —C(=NMe)NMe$_2$.

Nitro: —NO$_2$.

Nitroso: —NO.

Azido: —N$_3$.

Cyano (nitrile, carbonitrile): —CN.

Isocyano: —NC.

Cyanato: —OCN.

Isocyanato: —NCO.

Thiocyano (thiocyanato): —SCN.

Isothiocyano (isothiocyanato): —NCS.

Sulfhydryl (thiol, mercapto): —SH.

Thioether (sulfide): —SR, wherein R is a thioether substituent, for example, a C$_{1-7}$ alkyl group (also referred to as a C$_{1-7}$alkylthio group), a C$_{3-20}$ heterocyclyl group, or a C$_{5-20}$ aryl group, preferably a C$_{1-7}$ alkyl group. Examples of C$_{1-7}$ alkylthio groups include, but are not limited to, —SCH$_3$ and —SCH$_2$CH$_3$.

Disulfide: —SS—R, wherein R is a disulfide substituent, for example, a O$_{1-7}$ alkyl group, a C$_{3-20}$ heterocyclyl group, or a C$_{5-20}$ aryl group, preferably a O$_{1-7}$ alkyl group (also referred to herein as C$_{1-7}$ alkyl disulfide). Examples of C$_{1-7}$ alkyl disulfide groups include, but are not limited to, —SSCH$_3$ and —SSCH$_2$CH$_3$.

Sulfine (sulfinyl, sulfoxide): —S(=O)R, wherein R is a sulfine substituent, for example, a C$_{1-7}$ alkyl group, a C$_{3-20}$ heterocyclyl group, or a C$_{5-20}$ aryl group, preferably a C$_{1-7}$ alkyl group. Examples of sulfine groups include, but are not limited to, —S(=O)CH$_3$ and —S(=O)CH$_2$CH$_3$.

Sulfone (sulfonyl): —S(=O)$_2$R, wherein R is a sulfone substituent, for example, a C$_{1-7}$ alkyl group, a C$_{3-20}$ heterocyclyl group, or a C$_{5-20}$ aryl group, preferably a C$_{1-7}$ alkyl group, including, for example, a fluorinated or perfluorinated C$_{1-7}$ alkyl group. Examples of sulfone groups include, but are not limited to, —S(=O)$_2$CH$_3$ (methanesulfonyl, mesyl), —S(=O)$_2$CF$_3$ (triflyl), —S(=O)$_2$CH$_2$CH$_3$ (esyl), —S(=O)$_2$C$_4$F$_9$ (nonaflyl), —S(=O)$_2$CH$_2$CF$_3$ (tresyl), —S(=O)$_2$CH$_2$CH$_2$NH$_2$ (tauryl), —S(=O)$_2$Ph (phenylsulfonyl, besyl), 4-methylphenylsulfonyl (tosyl), 4-chlorophenylsulfonyl (closyl), 4-bromophenylsulfonyl (brosyl), 4-nitrophenyl (nosyl), 2-naphthalenesulfonate (napsyl), and 5-dimethylamino-naphthalen-1-ylsulfonate (dansyl).

Sulfinic acid (sulfino): —S(=O)OH, —SO$_2$H.

Sulfonic acid (sulfo): —S(=O)$_2$OH, —SO$_3$H.

Sulfinate (sulfinic acid ester): —S(=O)OR; wherein R is a sulfinate substituent, for example, a C$_{1-7}$ alkyl group, a C$_{3-20}$ heterocyclyl group, or a C$_{5-20}$ aryl group, preferably a C$_{1-7}$ alkyl group. Examples of sulfinate groups include, but are not limited to, —S(=O)OCH$_3$ (methoxysulfinyl; methyl sulfinate) and —S(=O)OCH$_2$CH$_3$ (ethoxysulfinyl; ethyl sulfinate).

Sulfonate (sulfonic acid ester): —S(=O)$_2$OR, wherein R is a sulfonate substituent, for example, a C$_{1-7}$ alkyl group, a C$_{3-20}$ heterocyclyl group, or a C$_{5-20}$ aryl group, preferably a C$_{1-7}$ alkyl group. Examples of sulfonate groups include, but are not limited to, —S(=O)$_2$OCH$_3$ (methoxysulfonyl; methyl sulfonate) and —S(=O)$_2$OCH$_2$CH$_3$ (ethoxysulfonyl; ethyl sulfonate).

Sulfinyloxy: —OS(=O)R, wherein R is a sulfinyloxy substituent, for example, a C$_{1-7}$ alkyl group, a C$_{3-20}$ heterocyclyl group, or a C$_{5-20}$ aryl group, preferably a C$_{1-7}$ alkyl group. Examples of sulfinyloxy groups include, but are not limited to, —OS(=O)CH$_3$ and —OS(=O)CH$_2$CH$_3$.

Sulfonyloxy: —OS(=O)$_2$R, wherein R is a sulfonyloxy substituent, for example, a C$_{1-7}$ alkyl group, a C$_{3-20}$ heterocyclyl group, or a C$_{5-20}$ aryl group, preferably a C$_{1-7}$ alkyl group. Examples of sulfonyloxy groups include, but are not limited to, —OS(=O)$_2$CH$_3$ (mesylate) and —OS(=O)$_2$CH$_2$CH$_3$ (esylate).

Sulfate: —OS(=O)$_2$OR; wherein R is a sulfate substituent, for example, a C$_{1-7}$ alkyl group, a C$_{3-20}$ heterocyclyl group, or a C$_{5-20}$ aryl group, preferably a C$_{1-7}$ alkyl group. Examples of sulfate groups include, but are not limited to, —OS(=O)$_2$OCH$_3$ and —SO(=O)$_2$OCH$_2$CH$_3$.

Sulfamyl (sulfamoyl; sulfinic acid amide; sulfinamide): —S(=O)NR$^1$R$^2$, wherein R$^1$ and R$^2$ are independently amino substituents, as defined for amino groups. Examples of sulfamyl groups include, but are not limited to, —S(=O)NH$_2$, —S(=O)NH(CH$_3$), —S(=O)N(CH$_3$)$_2$, —S(=O)NH(CH$_2$CH$_3$), —S(=O)N(CH$_2$CH$_3$)$_2$, and —S(=O)NHPh.

Sulfonamido (sulfinamoyl; sulfonic acid amide; sulfonamide): —S(=O)$_2$NR$^1$R$^2$, wherein R$^1$ and R$^2$ are independently amino substituents, as defined for amino groups. Examples of sulfonamido groups include, but are not limited to, —S(=O)$_2$NH$_2$, —S(=O)$_2$NH(CH$_3$), —S(=O)$_2$N(CH$_3$)$_2$, —S(=O)$_2$NH(CH$_2$CH$_3$), —S(=O)$_2$N(CH$_2$CH$_3$)$_2$, and —S(=O)$_2$NHPh.

Sulfamino: —NR$^1$S(=O)$_2$OH, wherein R$^1$ is an amino substituent, as defined for amino groups. Examples of sulfamino groups include, but are not limited to, —NHS(=O)$_2$OH and —N(CH$_3$)S(=O)$_2$OH.

Sulfonamino: —NR$^1$S(=O)$_2$R, wherein R$^1$ is an amino substituent, as defined for amino groups, and R is a sulfonamino substituent, for example, a C$_{1-7}$ alkyl group, a C$_{3-20}$ heterocyclyl group, or a C$_{5-20}$ aryl group, preferably a C$_{1-7}$ alkyl group. Examples of sulfonamino groups include, but are not limited to, —NHS(=O)$_2$CH$_3$ and —N(CH$_3$)S(=O)$_2$C$_6$H$_5$.

Sulfinamino: —NR$^1$S(=O)R, wherein R$^1$ is an amino substituent, as defined for amino groups, and R is a sulfinamino substituent, for example, a C$_{1-7}$ alkyl group, a C$_{3-20}$ heterocyclyl group, or a C$_{5-20}$ aryl group, preferably a C$_{1-7}$ alkyl group. Examples of sulfinamino groups include, but are not limited to, —NHS(=O)CH$_3$ and —N(CH$_3$)S(=O)C$_6$H$_5$.

Phosphino (phosphine): —PR$_2$, wherein R is a phosphino substituent, for example, —H, a C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphino groups include, but are not limited to, —PH$_2$, —P(CH$_3$)$_2$, —P(CH$_2$CH$_3$)$_2$, —P(t-Bu)$_2$, and —P(Ph)$_2$.

Phospho: —P(=O)$_2$.

Phosphinyl (phosphine oxide): —P(=O)R$_2$, wherein R is a phosphinyl substituent, for example, a C$_{1-7}$ alkyl group, a C$_{3-20}$ heterocyclyl group, or a C$_{5-20}$ aryl group, preferably a C$_{1-7}$ alkyl group or a C$_{5-20}$ aryl group. Examples of phosphinyl groups include, but are not limited to, —P(=O)(CH$_3$)$_2$, —P(=O)(CH$_2$CH$_3$)$_2$, —P(=O)(t-Bu)$_2$, and —P(=O)(Ph)$_2$.

Phosphonic acid (phosphono): —P(=O)(OH)$_2$.

Phosphonate (phosphono ester): —P(=O)(OR)$_2$, where R is a phosphonate substituent, for example, —H, a C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphonate groups include, but are not limited to, —P(=O)(OCH$_3$)$_2$, —P(=O)(OCH$_2$CH$_3$)$_2$, —P(=O)(O-t-Bu)$_2$, and —P(=O)(OPh)$_2$.

Phosphoric acid (phosphonooxy): —OP(=O)(OH)$_2$.

Phosphate (phosphonooxy ester): —OP(=O)(OR)$_2$, where R is a phosphate substituent, for example, —H, a C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphate groups include, but are not limited to, —OP(=O)(OCH$_3$)$_2$, —OP(=O)(OCH$_2$CH$_3$)$_2$, —OP(=O)(O-t-Bu)$_2$, and —OP(=O)(OPh)$_2$.

Phosphorous acid: —OP(OH)$_2$.

Phosphite: —OP(OR)$_2$, where R is a phosphite substituent, for example, —H, a C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphite groups include, but are not limited to, —OP(OCH$_3$)$_2$, —OP(OCH$_2$CH$_3$)$_2$, —OP(O-t-Bu)$_2$, and —OP(OPh)$_2$.

Phosphoramidite: —OP(OR$^1$)—NR$^2$$_2$, where R$^1$ and R$^2$ are phosphoramidite substituents, for example, —H, a (optionally substituted) C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphoramidite groups include, but are not limited to, —OP(OCH$_2$CH$_3$)—N(CH$_3$)$_2$, —OP(OCH$_2$CH$_3$)—N(i-Pr)$_2$, and —OP(OCH$_2$CH$_2$CN)—N(i-Pr)$_2$.

Phosphoramidate: —OP(=O)(OR$^1$)—NR$^2$$_2$, where R$^1$ and R$^2$ are phosphoramidate substituents, for example, —H, a (optionally substituted) C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphoramidate groups include, but are not limited to, —OP(=O)(OCH$_2$CH$_3$)—N(CH$_3$)$_2$, —OP(=O)(OCH$_2$CH$_3$)—N(i-Pr)$_2$, and —OP(=O)(OCH$_2$CH$_2$CN)—N(i-Pr)$_2$.

Includes Other Forms

Unless otherwise specified, included in the above are the well known ionic, salt, solvate, and protected forms of these substituents. For example, a reference to carboxylic acid (—COOH) also includes the anionic (carboxylate) form (—COO), a salt or solvate thereof, as well as conventional protected forms. Similarly, a reference to an amino group includes the protonated form (—N$^+$HR$^1$R$^2$), a salt or solvate of the amino group, for example, a hydrochloride salt, as well as conventional protected forms of an amino group. Similarly, a reference to a hydroxyl group also includes the anionic form (—O$^-$), a salt or solvate thereof, as well as conventional protected forms.

In one embodiment, compound (X) is used as a salt in the methods described herein. Compound (X) may be used as hydrochloride salt or a TFA salt, most preferably a hydrochloride salt.

Abbreviations

The following abbreviations are used in the specification:
BAIB [bis(acetoxy)iodo]benzene
Bn benzyl
DCM dichloromethane
DIPEA di-iso-propylethylamine
DMF N,N-dimethylformamide
DMSO dimethylsulfoxide
IPA iso-propyl alcohol
SEM 2-(trimethylsilyl)ethoxymethyl
TBAF tetrabutylammonium fluoride
TBS tert-butyldimethylsilyl
TCCA trichloroisocyanuric acid
TEMPO 2,2,6,6-tetramethylpiperidine-1-oxyl
TEA triethylamine
Tf triflate; trifluoromethanesulfonyl
TLC thin layer chromatography
TROC 2,2,2-trichloroethoxycarbonyl Experimental Details General Information Reaction progress was monitored by thin-layer chromatography (TLC) using Merck Kieselgel 60 F254 silica gel, with fluorescent indicator on aluminium plates. Visualisation of TLC was achieved with UV light or iodine vapour unless otherwise stated. Flash chromatography was performed using Merck Kieselgel 60 F254 silica gel. Extraction and chromatography solvents were bought and used without further purification from Fisher Scientific, U.K. All chemicals were purchased from Aldrich, Lancaster or BDH.

$^1$H and $^{13}$C NMR spectra were obtained on a Bruker Avance 400 spectrometer. Coupling constants are quoted in hertz (Hz). Chemical shifts are recorded in parts per million (ppm) downfield from tetramethylsilane. Spin multiplicities are described as s (singlet), bs (broad singlet), d (doublet), t (triplet), q (quartet), p (pentuplet) and m (multiplet). IR spectra were recorded on a Perkin-Elmer FT/IR paragon 1000 spectrophotometer by application of the sample in a solution of chloroform using the ATR "golden gate" system. Optical Rotations were measured at ambient temperature using a Bellingham and Stanley ADP 220 polarimeter. Mass spectrometry was performed on a ThermoQuest Navigator from Thermo Electron, Electrospray (ES) spectra were obtained at 20 to 30 V. Accurate mass measurements were performed using Micromass Q-TOF global tandem. All samples were run under electrospray ionization mode using 50% acetonitrile in water and 0.1% formic acid as a solvent. Samples were run on W mode which gives a typical resolution of 19000 at FWHH. The instrument was calibrated with [Glu]-Fibrinopeptide B immediately prior to measurement.

The LC/MS conditions were as follows: The HPLC (Waters Alliance 2695) was run using a mobile phase of water (A) (formic acid 0.1%) and acetonitrile (B) (formic acid 0.1%). Gradient: initial composition 5% B over 1.0 min then 5% B to 95% B within 3 min. The composition was held for 0.5 min at 95% B, and then returned to 5% B in 0.3 minutes. Total gradient run time equals 5 min. Flow rate 3.0 mL/min, 400 µL was split via a zero dead volume tee piece which passes into the mass spectrometer. Wavelength detection range: 220 to 400 nm. Function type: diode array (535 scans). Column: Phenomenex Onyx Monolithic C18 50×4.60 mm.

Preparation of Compounds (2) and (3)

Scheme 3

Compound (2)

(S)-1-(tert-Butoxycarbonyl)-4-oxopyrrolidine-2-carboxylic acid

Method: To an ice cooled solution of Boc hydroxyproline 1 (20 g, 86.4 mmol) in ethyl acetate (300 mL) were added a saturated aqueous solution of sodium metaperiodate (500 mL) and ruthenium oxide (115 mg, 0.864 mmol). The biphasic mixture was vigorously stirred at 35° C. for 6 h and monitored by LC/MS. When all the starting material was converted to product, as visible on the ES⁻ trace of the LC/MS, the two phases were allowed to separate. The aqueous layer was extracted with ethyl acetate (2×200 mL). The combined organic layers were washed with water (200 mL) and brine (100 mL), dried over magnesium sulfate and concentrated in vacuo. The residue was triturated with diethyl ether, retrieved by filtration and recrystallised in acetonitrile to give pure colorless crystals of the desired product 2 (8.90 g, 45%).

Analytical Data: LC/MS 2.12 min (ES−) m/z (relative intensity) 228 ([M−H]⁻, 100).

Known literature compound reported in: Narukawa Y., *Tetrahedron* 1997, 53, 539-556.

Compound (3)

(S)-4-Methylenepyrrolidine-2-carboxylic acid hydrochloride

Method: Solid potassium tert-butoxide (7.26 g, 64.7 mmol) was added portionwise to a suspension of methyltriphenylphosphonium bromide (26.4 g, 73.9 mmol) in dry THF (170 mL) at 0° C. (ice bath), under nitrogen. The yellow mixture was allowed to stir for 2 h and the ketone 2 (4.23 g, 18.5 mmol) was added as a solid. An exotherm was observed, and the reaction was found complete by LC/MS (visible only in the ES⁻ trace at 2.58 min showing a molecular ion at 226 ([M+H]⁻, 100)) after 25 min. The reaction mixture was extracted with saturated aqueous NaHCO₃ (150 mL) and washed with diethyl ether (2×200 mL). The aqueous extract was acidified with 1 N HCl to pH 1. The product was extracted diethyl ether and dried with brine and MgSO₄. Evaporation of diethyl ether gave the pure Boc protected acid as a colorless oil. This oil was immediately taken up in a 4N solution of HCl in dioxane (20 mL) and warmed gently with a hairdryer. A gas evolution was observed, followed by crystallisation of the product. Diethyl ether (150 mL) was added with stirring and the product 3 was retrieved by filtration, washed with diethyl ether, and dried in a desiccator under vacuum (2.75 g, 91%).

Analytical Data: LC/MS 0.36 min (ES+) m/z (relative intensity) 127.8 ([M+H]⁺, 100); $[\alpha]^{17}_D$=−28° (c=0.45, water); IR (ATR, neat) 2884, 1736, 1597, 1435, 1390, 1350, 1211, 1064, 973, 913, 834, 670 cm⁻¹; ¹H NMR (400 MHz, DMSO-d₆) δ 11.2-8.8 (m, 2H, NH), 5.28-5.01 (m, 2H), 4.43 (t, 1H, J=8.01 Hz), 3.82 (q, 2H, J=15.31 Hz), 2.95 (m, 1H), 2.68 (m, 1H).

Preparation of Compounds (5) and (6)

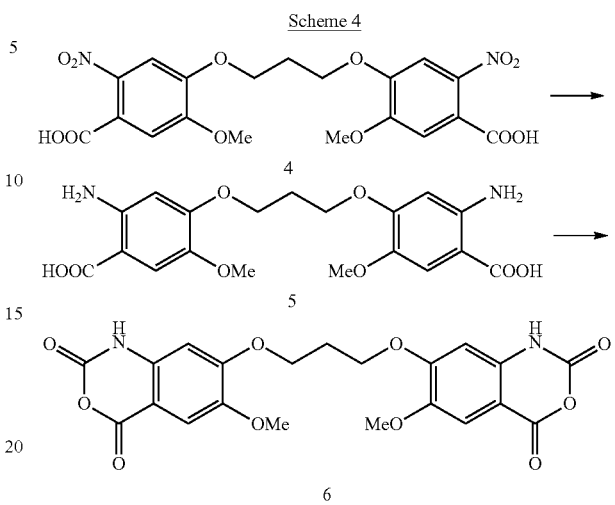

Scheme 4

Compound (5)

4,4'-(Propane-1,3-diylbis(oxy))bis(2-amino-5-methoxybenzoic acid)

Method: The bis-nitro acid 4 (23 g, 49.3 mmol) was partially dissolved in 0.5 N aqueous sodium hydroxide (2×200 mL in two hydrogenation flasks). Solid palladium on charcoal (10% w/w, 1.15 g per flask) was added in water and the reaction mixture was hydrogenated on a Parr apparatus at 45 PSI. When the hydrogen uptake had ceased, Pd/C was removed by filtration. The reaction was found to be complete by LC/MS. The pH of the filtrate was adjusted to 2-3 with 1N HCl under constant stirring and the resulting precipitate was retrieved by filtration. The solids were dried in a dessicator under vacuum, in the presence of the drying agent phosphorous pentoxide to yield the bis-anthranilic acid 5 (20 g, 100%).

Analytical Data: LC/MS 2.30 min (ES−) m/z (relative intensity) 404.92 ([M−H]⁻, 100); IR (ATR, neat) 1666, 1591, 1514, 1462, 1420, 1315, 1250, 1222, 1182, 1088, 1022, 967, 871, 758 cm⁻¹.

Compound (6)

7,7'-(Propane-1,3-diylbis(oxy))bis(6-methoxy-1H-benzo[d][1,3]oxazine-2,4-dione)

Method: Solid triphosgene (10 g, 33.7 mmol) was added portionwise rapidly to a suspension of finely pulverised bis anthranilic acid 5 (20 g, 40.6 mmol) in dry THF (100 mL). Pyridine (10 mL, 123 mmol) was added dropwise, the reaction was heated at reflux and progression was monitored by LC/MS. After 1 h, more triphosgene (10 g, 33.7 mmol) was added. Further triphosgene (5 g, 16.8 mmol) and pyridine (10 mL, 123 mmol) were added after 3 h. The reaction was deemed complete by LC/MS after 6 h. The product 6 was precipitated in excess water and ice, collected by filtration, washed with water and dried overnight in a desiccator (19.2 g, 85%).

Analytical Data: LC/MS 2.55 min (ES−) m/z (relative intensity) 457.18 ([M−H]⁺, 100); IR (ATR, neat) 1783, 1713, 1618, 1512, 1392, 1339, 1284, 1246, 1205, 1139, 1014, 989, 810, 750, 690, 642, 611 cm⁻¹.

Preparation of Compounds (7) and (8), and SJG-136
Scheme 5-Linear Approach
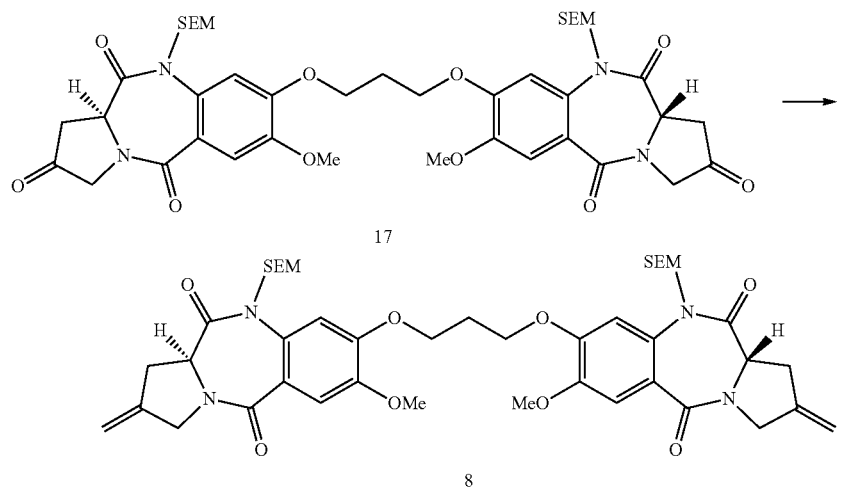
Scheme 6-Convergent Approach
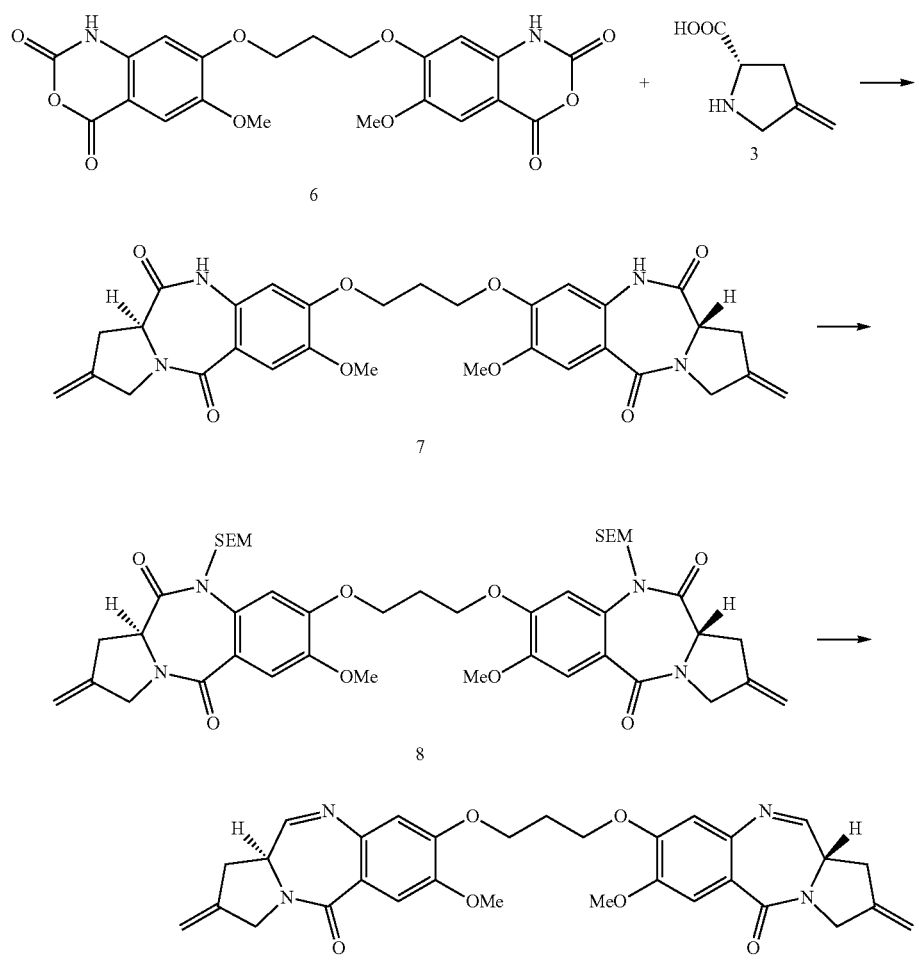

Compound (7)

1,1'-[[(Propane-1,3-diyl)dioxy]bis[(11aS)-7-methoxy-2-methylidene-1,2,3,10,11,11a-hexahydro-5H-pyrrolo[2,1c]-[1,4]benzodiazepin-5,11-dione]]

Method: DIPEA (3.12 mL, 17.9 mmol) was added to a suspension of finely divided bis-isatoic anhydride 6 (3.12 g, 6.8 mmol) and C-ring hydrochloride 3 (2.5 g, 15.3 mmol) in DMSO (12.5 mL). The mixture was heated to 120° C. (internal temperature) for 30 min. A vigorous gas evolution was initially observed, followed by dissolution of the reagents. After 30 min, LC/MS monitoring showed no improvement over time and the reaction mixture was worked-up by pouring in cold water (200 mL). The tan precipitate was retrieved by filtration and washed with water. The wet cake was further purified by digestion in refluxing acetonitrile (75 mL) followed by cooling to room temperature. The pale tan solid was retrieved by filtration, washed a small volume of diethyl ether, and dried in a vacuum oven at 40° C. (2.0 g, 50%).

Analytical Data: LC/MS 2.62 min (ES−) m/z (relative intensity) 587.27 ([M−H]−, 100); Analytical characteristics identical to previously published (Gregson et al., *J. Med. Chem.* 2001, 44, 1161-1174). However, the $[\alpha]_D$ value was found to be higher: $[\alpha]^{21}_D=+398°$ (c=0.3, HPLC CHCl$_3$) (lit $[\alpha]^{22}_D=+274°$ (c=0.06, CHCl$_3$)).

Compound (8)

1,1'-[[(Propane-1,3-diyl)dioxy]bis[(11aS)-7-methoxy-2-methylidene-10-((2-(trimethylsilyl)ethoxy)methyl)-1,2,3,10,11,11a-hexahydro-5H-pyrrolo[2,1c]-[1,4]benzodiazepin-5,11-dione]]

Method A: Solid bis-dilactam 7 (100 mg, 0.17 mmol) dried in a vacuum oven at 40° C. was suspended in anhydrous THF (10 mL) in an oven-dried 50 mL round-bottom flask, equipped with a dried septum and a nitrogen balloon. The suspension was cooled at −40° C. (acetonitrile/dry ice bath) and n-BuLi (1.6 M in hexane, 0.32 mL, 0.51 mmol) was added via syringe dropwise. A purple colour was observed. The suspension was allowed to stir for 1 h. Liquid SEM-Cl (0.09 mL, mmol) was syringed in dropwise and the suspension allowed to warm to room temperature slowly (3 h, leaving the bath). The reaction seemed almost complete by LC/MS at this point, and the mixture was allowed to stir overnight. The reaction mixture was extracted with DCM (30 mL) and washed with brine, followed by drying with magnesium sulphate. After evaporation of the solvent under vacuum, the crude residue was purified by flash chromatography (eluant 100% ethyl acetate, the product came quickly in the first few fractions) to give the desired product 8 (114 mg, 79%).

Method B: A solution of potassium-t-butoxide in anhydrous THF (0.5 M, 4.86 mL, 2.34 mmol, 4 eq) was added dropwise to a suspension of methyltriphenylphosphonium bromide (0.86 g, 2.4 mmol, 4.1 eq) in anhydrous THF (10 mL) at 0° C. under a Nitrogen atmosphere. The resultant yellow suspension was stirred at 0° C. for 1.5 h. The bis-ketone 17 (0.5 g, 0.59 mmol, 1 eq) in anhydrous THF (10 mL) was added dropwise to the yellow suspension and the mixture was allowed to reach room temperature with stirring over a period of 1 h. The reaction mixture was partitioned between EtOAc/H$_2$O (50 mL/50 mL) and the aqueous portion separated. The EtOAc portion was washed with saturated brine (50 mL), dried (MgSO$_4$) and evaporated under reduced pressure to give a brown oil. Purification by flash column chromatography (gradient elution: 90:10 v/v CHCl$_3$/EtOAc to 70:30 v/v n-CHCl$_3$/EtOAc) afforded the bis-methylene compound 8 as a colourless glass (0.28 g, 57%).

Analytical Data: LC/MS 3.90 min (ES+) m/z (relative intensity) 791 ([M+Na]+, 10); $^1$H NMR (400 MHz, CDCl$_3$) δ 7.333 (s, 2H), 7.327 (s, 2H), 5.48 (d, 2H, J=10 Hz), 5.17 (s, 2H), 5.10 (s, 2H), 4.69 (d, 2H, J=10 Hz), 4.4-4.14 (m, 10H), 3.89 (s, 6H), 3.8-3.7 (m, 2H), 3.7-3.6 (m, 2H), 3.45-3.4 (m, 2H), 2.85-2.75 (m, 2H), 2.43-2.39 (m, 2H), 0.99-0.93 (m, 4H), 0.005 (s, 18H); $^{13}$C NMR (100 MHz, CDCl$_3$) δ 171.08, 166.44, 152.61, 148.86, 143.26, 135.25, 123.31, 112.80, 110.20, 108.36, 79.38, 68.49, 66.86, 58.84, 57.51, 52.24, 33.68, 30.26, 19.66, 0.00.

SJG-136

1,1'-[[(Propane-1,3-diyl)dioxy]bis[(11aS)-7-methoxy-2-methylidene-1,2,3,11a-tetrahydro-5H-pyrrolo[2,1c]-[1,4]benzodiazepin-5-one]]

Method: Solid bis-SEM-dilactam 8 (100 mg, 0.12 mmol) was dissolved in a mixture of ethanol (3 mL) and THF (3 mL). Lithium borohydride (22 mg, 2.3 mmol) was added in one portion and the reaction mixture was allowed to stir for 1 h under nitrogen. LC/MS revealed completion of the reaction. The reaction mixture was partitioned between water (35 mL) and chloroform (50 mL). The organic phase was washed with water (35 mL), brine (35 mL), dried over magnesium sulphate and concentrated by rotary evaporation under vacuum. The residue was redissolved in a mixture of chloroform (2 mL), ethanol (2 mL) and water (2.5 mL). Silica gel (4 g) was added and the mixture was allowed to stir for 48 h. The mixture was filtered through a sinter funnel and washed with a mixture of chloroform/methanol (90:10 v/v). The filtrate was extracted with chloroform, washed with brine, dried over magnesium sulphate and concentrated by rotary-evaporation under vacuum. The residue was purified by flash chromatography (gradient elution: 100% CHCl$_3$ to 97:3 v/v CHCl$_3$/MeOH). The pure fractions were pulled and the solvent removed by rotary-evaporation under vacuum to give the desired product SJG-136 as a mixture of imine and carbinolamine methyl ethers. (46 mg, 70%).

Analytical Data: LC/MS 2.50 min (ES−) m/z (relative intensity) 555.06 ([M−H]−, 100); Analytical description identical to previously published by Gregson et al., *J. Med. Chem.* 2001, 44, 1161-1174. However, the $[\alpha]_D$ value was found to be higher than reported: $[\alpha]^{20}_D=+766°$ (c=0.37, HPLC CHCl$_3$) (lit $[\alpha]^{20}_D=+358°$ (c=0.07, CHCl$_3$)). This was expected, as the optical rotation measurement is very sensitive to the chloroform purity and the ratio of imine/carbinolamine adducts.

Preparation of Compounds (9) to (11) and (4)

A method for the synthesis of nitro-acid (4) from compound (9) via the compounds of formula (10) and (11) is disclosed in WO 00/012508 and WO 2006/111759. The preparation is illustrated below in Scheme 7.

Scheme 7

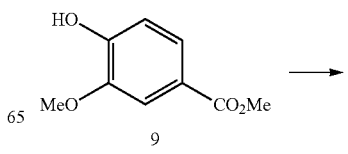

9

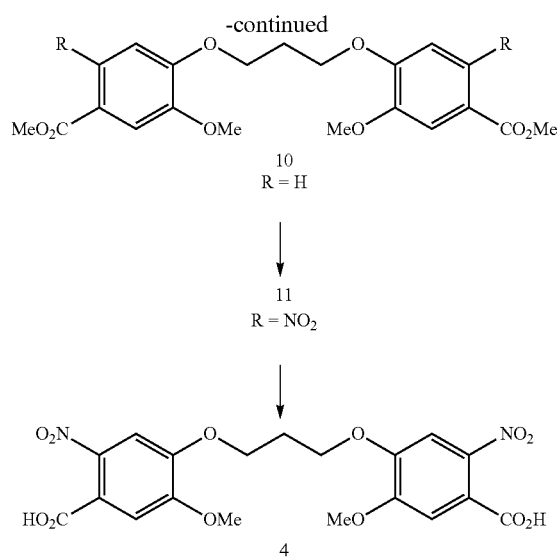

Preparation of Compounds (12) to (16)

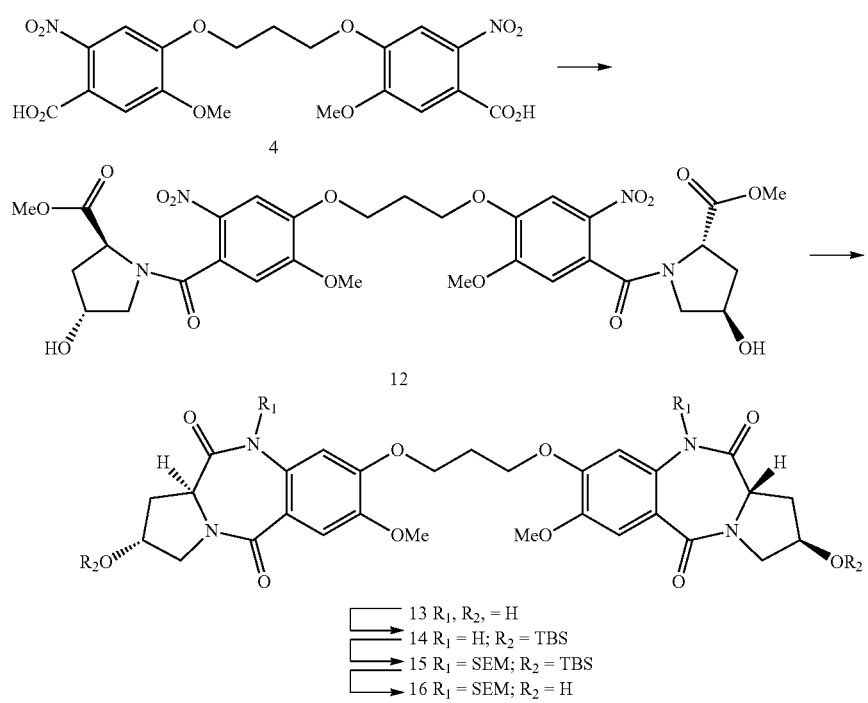

Compound (12)

1,1'-[[(Propane-1,3-diyl)dioxy]bis[(5-methoxy-2-nitro-1,4-phenylene)carbonyl]]bis[(2S,4R)-methyl-4-hydroxypyrrolidine-2-carboxylate]

Method A: A catalytic amount of DMF (2 drops) was added (effervescence!) to a stirred solution of the nitro-acid 4 (1.0 g, 2.15 mmol) and oxalyl chloride (0.95 mL, 1.36 g, 10.7 mmol) in dry THF (20 mL). The reaction mixture was allowed to stir for 16 hours at room temperature and the solvent was removed by evaporation in vacuo. The resulting residue was re-dissolved in dry THF (20 mL) and the acid chloride solution was added dropwise to a stirred mixture of (2S,4R)-methyl-4-hydroxypyrrolidine-2-carboxylate hydrochloride (859 mg, 4.73 mmol) and TEA (6.6 mL, 4.79 g, 47.3 mmol) in THF (10 mL) at −30° C. (dry ice/ethylene glycol) under a nitrogen atmosphere. The reaction mixture was allowed to warm to room temperature and stirred for a further 3 hours after which time TLC (95:5 v/v $CHCl_3$/MeOH) and LC/MS (2.45 min (ES+) m/z (relative intensity) 721 ($[M+H]^{+\cdot}$, 20)) revealed formation of product. Excess THF was removed by rotary evaporation and the resulting residue was dissolved in DCM (50 mL). The organic layer was washed with 1N HCl (2×15 mL), saturated $NaHCO_3$ (2×15 mL), $H_2O$ (20 mL), brine (30 mL) and dried ($MgSO_4$). Filtration and evaporation of the solvent gave the crude product as a dark coloured oil. Purification by flash chromatography (gradient elution: 100% $CHCl_3$ to 96:4 v/v $CHCl_3$/MeOH) isolated the pure amide 12 as an orange coloured glass (840 mg, 54%).

Method B: Oxalyl chloride (9.75 mL, 14.2 g, 111 mmol) was added to a stirred suspension of the nitro-acid 4 (17.3 g, 37.1 mmol) and DMF (2 mL) in anhydrous DCM (200 mL). Following initial effervescence the reaction suspension became a solution and the mixture was allowed to stir at room temperature for 16 hours. Conversion to the acid chloride was confirmed by treating a sample of the reaction mixture with MeOH and the resulting bis-methyl ester was observed by LC/MS. The majority of solvent was removed by evaporation in vacuo, the resulting concentrated solution was re-dissolved in a minimum amount of dry DCM and triturated with diethyl ether. The resulting yellow precipitate was collected by filtration, washed with cold diethyl ether and dried for 1 hour in a vacuum oven at 40° C. The solid acid chloride was added portionwise over a period of 25 minutes to a stirred suspension of (2S,4R)-methyl-4-hydroxypyrrolidine-2-carboxylate hydrochloride (15.2 g, 84.0 mmol) and TEA (25.7 mL, 18.7 g, 185 mmol) in DCM (150 mL) at −40° C. (dry ice/CH₃CN). Immediately, the reaction was complete as judged by LC/MS (2.47 min (ES+) m/z (relative intensity) 721 ([M+H]$^{+\cdot}$, 100)). The mixture was diluted with DCM (150 mL) and washed with 1N HCl (300 mL), saturated NaHCO₃ (300 mL), brine (300 mL), filtered (through a phase separator) and the solvent evaporated in vacuo to give the pure product 12 as an orange solid (21.8 g, 82%).

Analytical Data: $[\alpha]^{22}_D$=−46.1° (c=0.47, CHCl₃); ¹H NMR (400 MHz, CDCl₃) (rotamers) δ 7.63 (s, 2H), 6.82 (s, 2H), 4.79-4.72 (m, 2H), 4.49-4.28 (m, 6H), 3.96 (s, 6H), 3.79 (s, 6H), 3.46-3.38 (m, 2H), 3.02 (d, 2H, J=11.1 Hz), 2.48-2.30 (m, 4H), 2.29-2.04 (m, 4H); ¹³C NMR (100 MHz, CDCl₃) (rotamers) δ 172.4, 166.7, 154.6, 148.4, 137.2, 127.0, 109.7, 108.2, 69.7, 65.1, 57.4, 57.0, 56.7, 52.4, 37.8, 29.0; IR (ATR, CHCl₃) 3410 (br), 3010, 2953, 1741, 1622, 1577, 1519, 1455, 1429, 1334, 1274, 1211, 1177, 1072, 1050, 1008, 871 cm$^{-1}$; MS (ES⁺) m/z (relative intensity) 721 ([M+H]$^{+\cdot}$, 47), 388 (80); HRMS [M+H]$^{+\cdot}$ theoretical C₃₁H₃₆N₄O₁₆ m/z 721.2199, found (ES⁺) m/z 721.2227.
Compound (13)

1,1'-[[(Propane-1,3-diyl)dioxy]bis(11aS,2R)-2-(hydroxy)-7-methoxy-1,2,3,10,11,11a-hexahydro-5H-pyrrolo[2,1-c][1,4]-benzodiazepin-5,11-dione]

Method A: A suspension of 10% Pd/C (7.5 g, 10% w/w) in DMF (40 mL) was added to a solution of the nitro-ester 12 (75 g, 104 mmol) in DMF (360 mL). The suspension was hydrogenated in a Parr hydrogenation apparatus over 8 h. Progress of the reaction was monitored by LC/MS (2.12 min (ES+) m/z (relative intensity) 597 ([M+H]$^{+\cdot}$, 100), (ES−) m/z (relative intensity) 595 ([M+H]$^{+\cdot}$, 100) after the hydrogen uptake had stopped. Solid Pd/C was removed by filtration and the filtrate was concentrated by rotary evaporation under vacuum (below 10 mbar) at 40° C. to afford a dark oil containing traces of DMF and residual charcoal. The residue was digested in EtOH (500 mL) at 40° C. on a water bath (rotary evaporator bath) and the resulting suspension was filtered through celite and washed with ethanol (500 mL) to give a clear filtrate. Hydrazine hydrate (10 mL, 321 mmol) was added to the solution and the reaction mixture was heated at reflux. After 20 minutes the formation of a white precipitate was observed and reflux was allowed to continue for a further 30 minutes. The mixture was allowed to cool down to room temperature and the precipitate was retrieved by filtration, washed with diethyl ether (2*1 volume of precipitate) and dried in a vacuum desiccator to provide 13 (50 g, 81%).

Method B: A solution of the nitro-ester 12 (6.80 g, 9.44 mmol) in MeOH (300 mL) was added to Raney™ nickel (4 large spatula ends of a ~50% slurry in H₂O) and anti-bumping granules in a 3-neck round bottomed flask. The mixture was heated at reflux and then treated dropwise with a solution of hydrazine hydrate (5.88 mL, 6.05 g, 188 mmol) in MeOH (50 mL) at which point vigorous effervescence was observed. When the addition was complete (~30 minutes) additional Raney™ nickel was added carefully until effervescence had ceased and the initial yellow colour of the reaction mixture was discharged. The mixture was heated at reflux for a further 30 minutes at which point the reaction was deemed complete by TLC (90:10 v/v CHCl₃/MeOH) and LC/MS (2.12 min (ES+) m/z (relative intensity) 597 ([M+H]$^{+\cdot}$, 100)). The reaction mixture was allowed to cool to around 40° C. and then excess nickel removed by filtration through a sinter funnel without vacuum suction. The filtrate was reduced in volume by evaporation in vacuo at which point a colourless precipitate formed which was collected by filtration and dried in a vacuum desiccator to provide 13 (5.40 g, 96%).

Analytical Data: $[\alpha]^{27}_D$=+404° (c=0.10, DMF); ¹H NMR (400 MHz, DMSO-d₆) δ 10.2 (s, 2H, NH), 7.26 (s, 2H), 6.73 (s, 2H), 5.11 (d, 2H, J=3.98 Hz, OH), 4.32-4.27 (m, 2H), 4.19-4.07 (m, 6H), 3.78 (s, 6H), 3.62 (dd, 2H, J=12.1, 3.60 Hz), 3.43 (dd, 2H, J=12.0, 4.72 Hz), 2.67-2.57 (m, 2H), 2.26 (p, 2H, J=5.90 Hz), 1.99-1.89 (m, 2H); ¹³C NMR (100 MHz, DMSO-d₆) δ 169.1, 164.0, 149.9, 144.5, 129.8, 117.1, 111.3, 104.5, 54.8, 54.4, 53.1, 33.5, 27.5; IR (ATR, neat) 3438, 1680, 1654, 1610, 1605, 1516, 1490, 1434, 1379, 1263, 1234, 1216, 1177, 1156, 1115, 1089, 1038, 1018, 952, 870 cm$^{-1}$; MS (ES⁺) m/z (relative intensity) 619 ([M+Na]$^{+\cdot}$, 10), 597 ([M+H]$^{+\cdot}$, 52), 445 (12), 326 (11); HRMS [M+H]$^{+\cdot}$ theoretical C₂₉H₃₂N₄O₁₀ m/z 597.2191, found (ES⁺) m/z 597.2205.
Compound (14)

1,1'-[[(Propane-1,3-diyl)dioxy]bis(11aS,2R)-2-(tert-butyldimethylsilyloxy)-7-methoxy-1,2,3,10,11,11a-hexahydro-5H-pyrrolo[2,1-c][1,4]-benzodiazepin-5,11-dione]

TBSCI (317 mg, 2.1 mmol) and imidazole (342 mg, 5.03 mmol) were added to a cloudy solution of the tetralactam 13 (250 mg, 0.42 mmol) in anhydrous DMF (6 mL). The mixture was allowed to stir under a nitrogen atmosphere for 3 h after which time the reaction was deemed complete as judged by LC/MS (3.90 min (ES+) m/z (relative intensity) 825 ([M+H]$^{+\cdot}$, 100)). The reaction mixture was poured onto ice (~25 mL) and allowed to warm to room temperature with stirring. The resulting white precipitate was collected by vacuum filtration, washed with H₂O, diethyl ether and dried in the vacuum desiccator to provide pure 14 (252 mg, 73%).

Analytical Data: $[\alpha]^{23}_D$=+234° (c=0.41, CHCl₃); ¹H NMR (400 MHz, CDCl₃) δ 8.65 (s, 2H, NH), 7.44 (s, 2H), 6.54 (s, 2H), 4.50 (p, 2H, J=5.38 Hz), 4.21-4.10 (m, 6H), 3.87 (s, 6H), 3.73-3.63 (m, 4H), 2.85-2.79 (m, 2H), 2.36-2.29 (m, 2H), 2.07-1.99 (m, 2H), 0.86 (s, 18H), 0.08 (s, 12H); ¹³C NMR (100 MHz, CDCl₃) δ 170.4, 165.7, 151.4, 146.6, 129.7, 118.9, 112.8, 105.3, 69.2, 65.4, 56.3, 55.7, 54.2, 35.2, 28.7, 25.7, 18.0, −4.82 and −4.86; IR (ATR, CHCl₃) 3235, 2955, 2926, 2855, 1698, 1695, 1603, 1518, 1491, 1446, 1380, 1356, 1251, 1220, 1120, 1099, 1033 cm$^{-1}$; MS (ES⁺) m/z (relative intensity) 825 ([M+H]$^{+\cdot}$, 62), 721 (14), 440 (38); HRMS [M+H]$^{+\cdot}$ theoretical C₄₁H₆₀N₄O₁₀Si₂ m/z 825.3921, found (ES⁺) m/z 825.3948.
Compound (15)

1,1'-[[(Propane-1,3-diyl)dioxy]bis(11aS,2R)-2-(tert-butyldimethylsilyloxy)-7-methoxy-10-((2-(trimethylsilyl)ethoxy)methyl)-1,2,3,10,11,11a-hexahydro-5H-pyrrolo[2,1-c][1,4]-benzodiazepin-5,1'-dione]

A solution of n-BuLi (4.17 mL of a 1.6 M solution in hexane, 6.67 mmol) in anhydrous THF (10 mL) was added dropwise to a stirred suspension of the tetralactam 14 (2.20 g, 2.67 mmol) in anhydrous THF (30 mL) at −30° C. (dry ice/ethylene glycol) under a nitrogen atmosphere. The reaction mixture was allowed to stir at this temperature for 1 hour (now a reddish orange colour) at which point a solution of SEMCl (1.18 mL, 1.11 g, 6.67 mmol) in anhydrous THF (10 mL) was added dropwise. The reaction mixture was allowed to slowly warm to room temperature and was stirred for 16 hours under a nitrogen atmosphere. The reaction was deemed complete as judged by TLC (EtOAc) and LC/MS (4.77 min (ES+) m/z (relative intensity) 1085 ([M+H]$^{+\cdot}$, 100)). The THF was removed by evaporation in vacuo and the resulting residue dissolved in EtOAc (60 mL), washed with H$_2$O (20 mL), brine (20 mL), dried (MgSO$_4$) filtered and evaporated in vacuo to provide the crude product. Purification by flash chromatography (80:20 v/v Hexane/EtOAc) gave the pure N10-SEM-protected tetralactam 15 as an oil (2.37 g, 82%).

Analytical Data: $[\alpha]^{23}_D$=+163° (c=0.41, CHCl$_3$); $^1$H NMR (400 MHz, CDCl$_3$) δ 7.33 (s, 2H), 7.22 (s, 2H), 5.47 (d, 2H, J=9.98 Hz), 4.68 (d, 2H, J=9.99 Hz), 4.57 (p, 2H, J=5.77 Hz), 4.29-4.19 (m, 6H), 3.89 (s, 6H), 3.79-3.51 (m, 8H), 2.87-2.81 (m, 2H), 2.41 (p, 2H, J=5.81 Hz), 2.03-1.90 (m, 2H), 1.02-0.81 (m, 22H), 0.09 (s, 12H), 0.01 (s, 18H); $^{13}$C NMR (100 MHz, CDCl$_3$) δ 170.0, 165.7, 151.2, 147.5, 133.8, 121.8, 111.6, 106.9, 78.1, 69.6, 67.1, 65.5, 56.6, 56.3, 53.7, 35.6, 30.0, 25.8, 18.4, 18.1, −1.24, −4.73; IR (ATR, CHCl$_3$) 2951, 1685, 1640, 1606, 1517, 1462, 1433, 1360, 1247, 1127, 1065 cm$^{-1}$; MS (ES$^+$) m/z (relative intensity) 1113 ([M+Na]$^{+\cdot}$, 48), 1085 ([M+H]$^{+\cdot}$, 100), 1009 (5), 813 (6); HRMS [M+H]$^{+\cdot}$ theoretical C$_{53}$H$_{88}$N$_4$O$_{12}$Si$_4$ m/z 1085.5548, found (ES$^+$) m/z 1085.5542.

Compound (16)

1,1'-[[(Propane-1,3-diyl)dioxy]bis(11aS,2R)-2-hydroxy-7-methoxy-10-((2-(trimethylsilyl)ethoxy)methyl)-1,2,3,10,11,11a-hexahydro-5H-pyrrolo[2,1-c][1,4]-benzodiazepin-5,11-dione]

A solution of TBAF (5.24 mL of a 1.0 M solution in THF, 5.24 mmol) was added to a stirred solution of the bis-silyl ether 15 (2.58 g, 2.38 mmol) in THF (40 mL) at room temperature. After stirring for 3.5 hours, analysis of the reaction mixture by TLC (95:5 v/v CHCl$_3$/MeOH) revealed completion of reaction. The reaction mixture was poured into a solution of saturated NH$_4$Cl (100 mL) and extracted with EtOAc (3×30 mL). The combined organic layers were washed with brine (60 mL), dried (MgSO$_4$), filtered and evaporated in vacuo to provide the crude product. Purification by flash chromatography (gradient elution: 100% CHCl$_3$ to 96:4 v/v CHCl$_3$/MeOH) gave the pure tetralactam 16 as a white foam (1.78 g, 87%).

Analytical Data: LC/MS 3.33 min (ES+) m/z (relative intensity) 879 ([M+Na]$^{+\cdot}$, 100), 857 ([M+H]$^{+\cdot}$, 40); $[\alpha]^{23}_D$=+202° (c=0.34, CHCl$_3$); $^1$H NMR (400 MHz, CDCl$_3$) δ 7.28 (s, 2H), 7.20 (s, 2H), 5.44 (d, 2H, J=10.0 Hz), 4.72 (d, 2H, J=10.0 Hz), 4.61-4.58 (m, 2H), 4.25 (t, 4H, J=5.83 Hz), 4.20-4.16 (m, 2H), 3.91-3.85 (m, 8H), 3.77-3.54 (m, 6H), 3.01 (br s, 2H, OH), 2.96-2.90 (m, 2H), 2.38 (p, 2H, J=5.77 Hz), 2.11-2.05 (m, 2H), 1.00-0.91 (m, 4H), 0.00 (s, 18H); $^{13}$C NMR (100 MHz, CDCl$_3$) δ 169.5, 165.9, 151.3, 147.4, 133.7, 121.5, 111.6, 106.9, 79.4, 69.3, 67.2, 65.2, 56.5, 56.2, 54.1, 35.2, 29.1, 18.4, −1.23; IR (ATR, CHCl$_3$) 2956, 1684, 1625, 1604, 1518, 1464, 1434, 1361, 1238, 1058, 1021 cm$^{-1}$; MS (ES$^+$) m/z (relative intensity) 885 ([M+29]$^{+\cdot}$, 70), 857 ([M+H]$^{+\cdot}$, 100), 711 (8), 448 (17); HRMS [M+H]$^+$ theoretical C$_{41}$H$_{60}$N$_4$O$_{12}$Si$_2$ m/z 857.3819, found (ES$^+$) m/z 857.3826.

Preparation of Compound (8) and SJG-136

Scheme 9

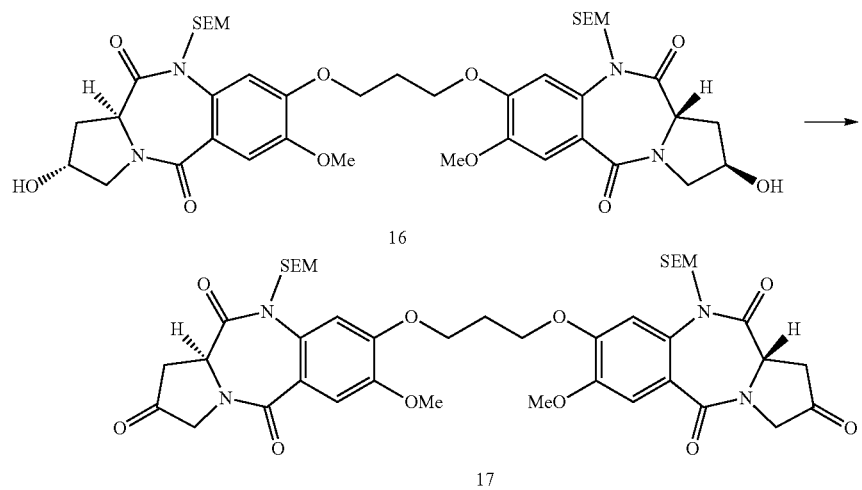

Compound (17)

1,1'-[[(Propane-1,3-diyl)dioxy]bis[(11aS)-7-methoxy-2-oxo-10-((2-(trimethylsilyl)ethoxy)methyl)1,2,3,10,11,11a-hexahydro-5H-pyrrolo[2,1-c][1,4]benzodiazepin-5,11-dione]]

Method A: Solid TCCA (10.6 g, 45.6 mmol) was added portionwise to a stirred solution of the alcohol 16 (18.05 g, 21.1 mmol) and TEMPO (123 mg, 0.78 mmol) in anhydrous DCM (700 mL) at 0° C. (ice/acetone). The reaction mixture was stirred at 0° C. under a nitrogen atmosphere for 15 min after which time TLC (EtOAc) and LC/MS [3.57 min (ES+) m/z (relative intensity) 875 ([M+Na]$^{+\cdot}$, 50)] revealed completion of reaction. The reaction mixture was filtered through celite and the filtrate was washed with saturated aqueous NaHCO$_3$ (400 mL), brine (400 mL), dried (MgSO$_4$), filtered and evaporated in vacuo to provide the crude product. Purification by flash column chromatography (80:20 v/v EtOAc/Hexane) afforded the bis-ketone 17 as a foam (11.7 g, 65%).

Method B: A solution of anhydrous DMSO (0.72 mL, 0.84 g, 10.5 mmol) in dry DCM (18 mL) was added dropwise over a period of 25 min to a stirred solution of oxalyl chloride (2.63 mL of a 2.0 M solution in DCM, 5.26 mmol) under a nitrogen atmosphere at −60° C. (liq N$_2$/CHCl$_3$). After stirring at −55° C. for 20 min, a slurry of the substrate 16 (1.5 g, 1.75 mmol) in dry DCM (36 mL) was added dropwise over a period of 30 min to the reaction mixture. After stirring for a further 50 min at −55° C., a solution of TEA (3.42 mL, 2.49 g; 24.6 mmol) in dry DCM (18 mL) was added dropwise over a period of 20 min to the reaction mixture. The stirred reaction mixture was allowed to warm to room temperature (~1.5 h) and then diluted with DCM (50 mL). The organic solution was washed with 1 N HCl (2×25 mL), $H_2O$ (30 mL), brine (30 mL) and dried ($MgSO_4$). Filtration and evaporation of the solvent in vacuo afforded the crude product which was purified by flash column chromatography (80:20 v/v EtOAc/Hexane) to afford bis-ketone 17 as a foam (835 mg, 56%).

Analytical Data: LC/MS 3.55 min (ES+) m/z (relative intensity) 875 ([M+Na]$^{+\cdot}$, 50); $[\alpha]^{20}_D$=+291° (c=0.26, $CHCl_3$); $^1H$ NMR (400 MHz, $CDCl_3$) δ 7.32 (s, 2H), 7.25 (s, 2H), 5.50 (d, 2H, J=10.1 Hz), 4.75 (d, 2H, J=10.1 Hz), 4.60 (dd, 2H, J=9.85, 3.07 Hz), 4.31-4.18 (m, 6H), 3.89-3.84 (m, 8H), 3.78-3.62 (m, 4H), 3.55 (dd, 2H, J=19.2, 2.85 Hz), 2.76 (dd, 2H, J=19.2, 9.90 Hz), 2.42 (p, 2H, J=5.77 Hz), 0.98-0.91 (m, 4H), 0.00 (s, 18H); $^{13}C$ NMR (100 MHz, $CDCl_3$) δ 206.8, 168.8, 165.9, 151.8, 148.0, 133.9, 120.9, 111.6, 107.2, 78.2, 67.3, 65.6, 56.3, 54.9, 52.4, 37.4, 29.0, 18.4, −1.24; IR (ATR, $CHCl_3$) 2957, 1763, 1685, 1644, 1606, 1516, 1457, 1434, 1360, 1247, 1209, 1098, 1066, 1023 $cm^{-1}$; MS (ES$^+$) m/z (relative intensity) 881 ([M+29]$^{+\cdot}$, 38), 853 ([M+H]$^{+\cdot}$, 100), 707 (8), 542 (12); HRMS [M+H]$^{+\cdot}$ theoretical $C_{41}H_{36}N_4O_{12}Si_2$ m/z 853.3506, found (ES$^+$) m/z 853.3502.

References

The following references are incorporated by reference in their entirety:

WO 95/04718
WO 00/12508
WO 2004/043963
WO 2005/042535
WO 2005/085251
WO 2006/111759
WO 2007/085930
Japanese Patent 58-180 487
US 2007/185336
Antonow et al *J. Comb. Chem.*, 2007, 9, 437-445.
Arima, et al., *J. Antibiotics*, 25, 437-444 (1972).
Bose, et al., *Tetrahedron*, 48, 751-758 (1992).
Cooper, N., *Design, Synthesis and Evaluation of Novel C2-Aryl Pyrrolobenzodiazepines as Potential Anticancer Agents*, Thesis submitted to School of Pharmacy, University of London, dated 5 Oct. 2006.
Gregson et al., *Chem. Commun.* 1999, 797-798.
Gregson et al., *J. Med. Chem.* 2001, 44, 1161-1174.
Hara, et al., *J. Antibiotics*, 41, 702-704 (1988).
Hochlowski, et al., *J. Antibiotics*, 40, 145-148 (1987).
Hurley and Needham-VanDevanter, *Acc. Chem. Res.*, 19, 230-237 (1986).
Itoh, et al., *J. Antibiotics*, 41, 1281-1284 (1988).
Kohn, in *Antibiotics III*. Springer-Verlag, New York, pp. 3-11 (1975).
Konishi, et al., *J. Antibiotics*, 37, 200-206 (1984).
Kuminoto, et al., *J. Antibiotics*, 33, 665-667 (1980).
Langley and Thurston, *J. Org. Chem.*, 52, 91-97 (1987).
Leber, et al., *J. Am. Chem. Soc.*, 110, 2992-2993 (1988).
Leimgruber, et al., *J. Am. Chem. Soc.*, 87, 5793-5795 (1965).
Leimgruber, et al., *J. Am. Chem. Soc.*, 87, 5791-5793 (1965).
Narukawa Y., *Tetrahedron* 1997, 53, 539-556.
Shimizu, et al., *J. Antibiotics*, 29, 2492-2503 (1982).
Takeuchi, et al., *J. Antibiotics*, 29, 93-96 (1976).
Thomas Fey et al, *J. Org. Chem.*, 2001, 66, 8154-8159.
Thurston, et al., *Chem. Brit.*, 26, 767-772 (1990).
Thurston, et al., *Chem. Rev.* 1994, 433-465 (1994).
Tsunakawa, et al., *J. Antibiotics*, 41, 1366-1373 (1988).

The invention claimed is:

1. A compound of formula (S):

wherein:

SEM is 2-(trimethylsilyl)ethoxymethyl;

$R^2$ is $CHR^{2A}$, and $R^{2A}$ is independently selected from H, R, $CO_2R$, COR, CHO, $CO_2H$, and halo;

$R^6$ and $R^9$ are independently selected from H, R, OH, OR, SH, SR, $NH_2$, NHR, NRR', $NO_2$, $Me_3Sn$ and halo;

$R^7$ is independently selected from H, R, OH, OR, SH, SR, $NH_2$, NHR, NRR', $NO_2$, $Me_3Sn$ and halo;

or the adjacent groups $R^6$ and $R^7$ together form a group —O—$(CH_2)_p$—O—, where p is 1 or 2; and R is independently selected from optionally substituted $C_{1-12}$ alkyl, $C_{3-7}$ heterocyclyl and $C_{5-20}$ aryl groups, wherein the optional substituents are selected from $C_{1-7}$ alkyl, $C_{3-7}$ heterocyclyl, $C_{5-20}$ aryl, halo, hydroxy, $C_{1-7}$ alkoxy, $C_{3-7}$ heterocyclyloxy, and $C_{5-20}$ aryloxy;

R" is a $C_{3-12}$ alkylene group, which chain may be interrupted by one or more heteroatoms selected from O, S and N(H); and/or aromatic rings;

each X is independently selected from O, S, or N(H); and $R^{2'}$, $R^{6'}$, $R^{7'}$, $R^{9'}$, and X' are independently selected from the same groups as $R^2$, $R^6$, $R^7$, $R^9$, and X respectively; and wherein $C_{3-7}$ heterocyclyl pertains to a monovalent moiety obtained by removing a hydrogen atom from a ring atom of a heterocyclic compound, which moiety has from 3 to 7 ring atoms, of which from 1 to 4 are ring heteroatoms, selected from N, O and S.

2. The compound according to claim 1, wherein $R^{2A}$ is independently selected from H and R.

3. The compound according to claim 2, wherein $R^{2A}$ is independently H.

4. The compound according to claim 1, wherein $R^7$ and $R^{7'}$ are each independently OR.

5. The compound according to claim 4, wherein $R^7$ and $R^{7'}$ are each independently OMe.

6. The compound according to claim 1, wherein $R^6$ and $R^{6'}$ are each independently H.

7. The compound according to claim 1, wherein $R^9$ and $R^{9'}$ are each independently H.

8. The compound according to claim 1, wherein X and X' are each independently O.

9. The compound according to claim 1, wherein R" is a $C_{3-12}$ alkylene group.

10. The compound according to claim 9, wherein R" is selected from a $C_3$ alkylene group and a $C_5$ alkylene group.

11. The compound according to claim 10, wherein R" is a $C_3$ alkylene group.

12. The compound according to claim 1 of formula (8):

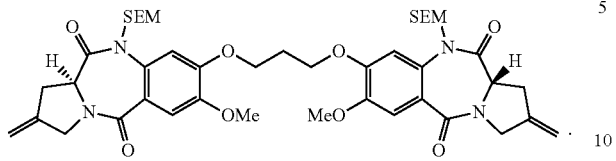

13. A process for the preparation of a compound of formula (A), the process comprising the step of reacting a compound of formula (S) with a reducing agent, wherein the compound of formula (S) is:

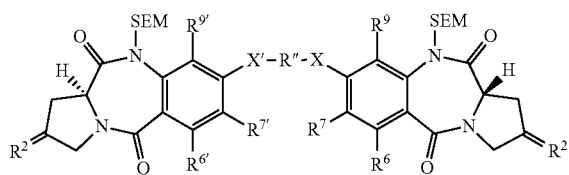

wherein:
SEM is 2-(trimethylsilyl)ethoxymethyl;
$R^2$ is $CHR^{2A}$, and $R^{2A}$ is independently selected from H, R, $CO_2R$, COR, CHO, $CO_2H$, and halo;
$R^6$ and $R^9$ are independently selected from H, R, OH, OR, SH, SR, $NH_2$, NHR, NRR', $NO_2$, $Me_3Sn$ and halo;
$R^7$ is independently selected from H, R, OH, OR, SH, SR, $NH_2$, NHR, NRR', $NO_2$, $Me_3Sn$ and halo;
or the adjacent groups $R^6$ and $R^7$ together form a group —O—$(CH_2)_p$—O—, where p is 1 or 2; and
R is independently selected from optionally substituted $C_{1-12}$ alkyl, $C_{3-7}$ heterocyclyl and $C_{5-20}$ aryl groups, wherein the optional substituents are selected from $C_{1-7}$ alkyl, $C_{3-7}$ heterocyclyl, $C_{5-20}$ aryl, halo, hydroxy, $C_{1-7}$ alkoxy, $C_{3-20}$ heterocyclyloxy, and $C_{5-20}$ aryloxy;
R" is a $C_{3-12}$ alkylene group, which chain may be interrupted by one or more heteroatoms selected from O, S and N(H) and/or aromatic rings;
each X is independently selected from O, S, or N(H); and
$R^{2'}$, $R^{6'}$, $R^{7'}$, $R^{9'}$, and X' are independently selected from the same groups as $R^2$, $R^6$, $R^7$, $R^9$, and X respectively; and
wherein $C_{3-7}$ heterocyclyl pertains to a monovalent moiety obtained by removing a hydrogen atom from a ring atom of a heterocyclic compound, which moiety has from 3 to 7 ring atoms, of which from 1 to 4 are ring heteroatoms, selected from N, O and S; and (A) is a compound:

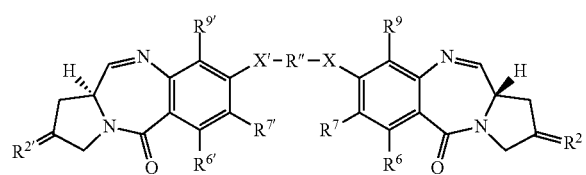

where $R^{2'}$, $R^{6'}$, $R^{7'}$, $R^{9'}$, X', R", $R^2$, $R^6$, $R^7$, $R^9$, and X are as defined for the compounds of formula (S).

14. The process according to claim 13, wherein the reducing agent is a borohydride salt.

15. A process for the preparation of a compound of formula (S), the process comprising the step of protecting the amide nitrogens of (B) with SEM, wherein the compound of formula (S) is:

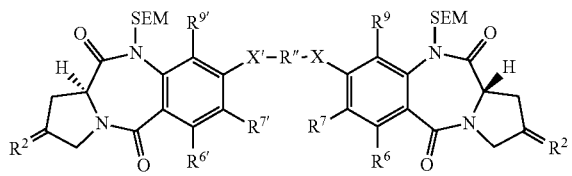

wherein:
SEM is 2-(trimethylsilyl)ethoxymethyl;
$R^2$ is $CHR^{2A}$, and $R^{2A}$ is independently selected from H, R, $CO_2R$, COR, CHO, $CO_2H$, and halo;
$R^6$ and $R^9$ are independently selected from H, R, OH, OR, SH, SR, $NH_2$, NHR, NRR', $NO_2$, $Me_3Sn$ and halo;
$R^7$ is independently selected from H, R, OH, OR, SH, SR, $NH_2$, NHR, NRR', $NO_2$, $Me_3Sn$ and halo;
or the adjacent groups $R^6$ and $R^7$ together form a group —O—$(CH_2)_p$—O—, where p is 1 or 2; and
R is independently selected from optionally substituted $C_{1-12}$ alkyl, $C_{3-7}$ heterocyclyl and $C_{5-20}$ aryl groups, wherein the optional substituents are selected from $C_{1-7}$ alkyl, $C_{3-7}$ heterocyclyl, $C_{5-20}$ aryl, halo, hydroxy, $C_{1-7}$ alkoxy, $C_{3-20}$ heterocyclyloxy, and $C_{5-20}$ aryloxy; R" is a $C_{3-12}$ alkylene group, which chain may be interrupted by one or more heteroatoms selected from O, S and N(H) and/or aromatic rings;
each X is independently selected from O, S, or N(H); and
$R^{2'}$, $R^{6'}$, $R^{7'}$, $R^{9'}$, and X' are independently selected from the same groups as $R^2$, $R^6$, $R^7$, $R^9$, and X respectively; and
wherein $C_{3-7}$ heterocyclyl pertains to a monovalent moiety obtained by removing a hydrogen atom from a ring atom of a heterocyclic compound, which moiety has from 3 to 7 ring atoms, of which from 1 to 4 are ring heteroatoms, selected from N, O and S; and B is a compound:

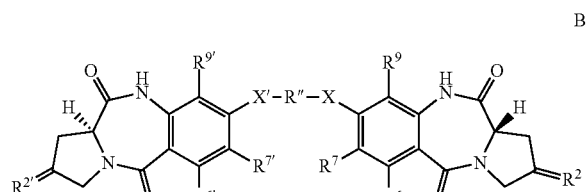

where $R^{2'}$, $R^{6'}$, $R^{7'}$, $R^{9'}$, X', R", $R^2$, $R^6$, $R^7$, $R^9$, and X are as defined for the compound of formula (S).

16. The process according to claim 15, wherein (B) is reacted with SEM-Cl thereby to form (S).

17. A process for the preparation of a compound formula (B)

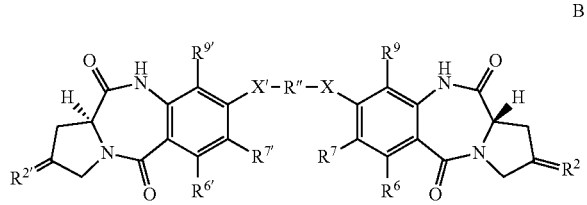

wherein:
- $R^2$ is $CHR^{2A}$, and $R^{2A}$ is independently selected from H, R, $CO_2R$, COR, CHO, $CO_2H$, and halo;
- $R^6$ and $R^9$ are independently selected from H, R, OH, OR, SH, SR, $NH_2$, NHR, NRR', $NO_2$, $Me_3Sn$ and halo;
- $R^7$ is independently selected from H, R, OH, OR, SH, SR, $NH_2$, NHR, NRR', $NO_2$, $Me_3Sn$ and halo;
- or the adjacent groups $R^6$ and $R^7$ together form a group —O—$(CH_2)_p$—O—, where p is 1 or 2; and
- R is independently selected from optionally substituted $C_{1-12}$ alkyl, $C_{3-7}$ heterocyclyl and $C_{5-20}$ aryl groups, wherein the optional substituents are selected from $C_{1-7}$ alkyl, $C_{3-7}$ heterocyclyl, $C_{5-20}$ aryl, halo, hydroxy, $C_{1-7}$ alkoxy, $C_{3-20}$ heterocyclyloxy, and $C_{5-20}$ aryloxy;
- R" is a $C_{3-12}$ alkylene group, which chain may be interrupted by one or more heteroatoms selected from O, S and N(H) and/or aromatic rings;
- each X is independently selected from O, S, or N(H); and
- $R^{2'}$, $R^{6'}$, $R^{7'}$, $R^{9'}$, and X' are independently selected from the same groups as $R^2$, $R^6$, $R^7$, $R^9$, and X respectively; and
- wherein $C_{3-7}$ heterocyclyl pertains to a monovalent moiety obtained by removing a hydrogen atom from a ring atom of a heterocyclic compound, which moiety has from 3 to 7 ring atoms, of which from 1 to 4 are ring heteroatoms, selected from N, O and S;

the process comprising the step of reacting a compound of formula (X) with a compound of formula (C), and (X) and (C) are:

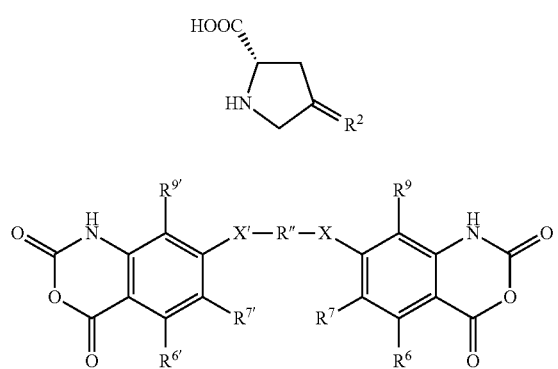

where $R^b$, R', $R^9$, X', R", R', $R^b$, R', $R^9$, and X are as defined for the compounds of formula (B).

18. The process according claim 17, wherein (C) is compound (6):

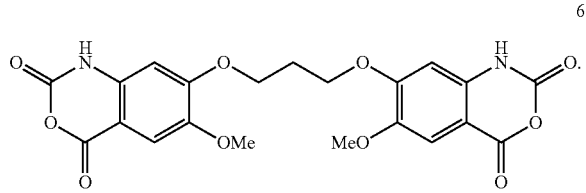 [SMILES: COc1cc2c(=O)oc(=O)[nH]c2cc1OCCCOc1cc2[nH]c(=O)oc(=O)c2cc1OC]

19. The process according to claim 17, wherein (X) is compound (3):

20. The process according to claim 15 further comprising the preceding step of reacting a compound of formula (X) with a compound of formula (C), wherein (B) is as defined in claim 15, and (X) and (C) are:

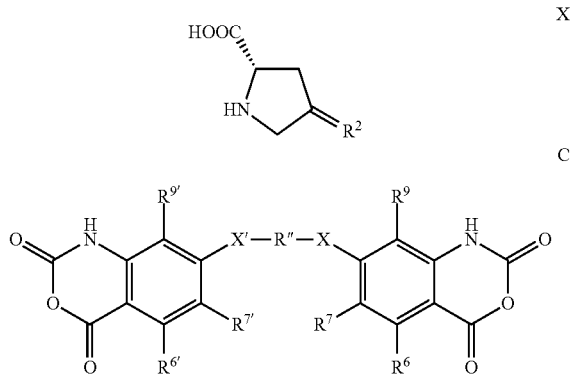

and $R^{6'}$, $R^{7'}$, $R^{9'}$, X', R", $R^2$, $R^6$, $R^7$, $R^9$, and X are as defined for the compounds of formula (B).

21. The process according to claim 13, further comprising the preceding step of protecting the amide nitrogens of (B) with SEM,
wherein B is a compound:

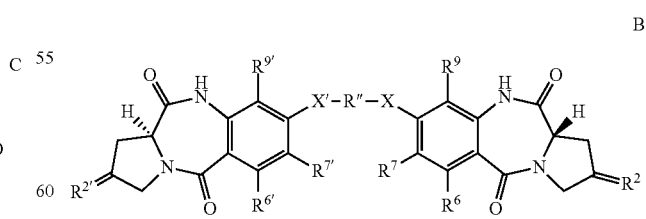

wherein $R^{2'}$, $R^{6'}$, $R^{7'}$, $R^{9'}$, X', R", $R^2$, $R^6$, $R^7$, $R^9$, and X are as defined for the compound of formula (S);
and optionally the preceding step of reacting a compound of formula (X) with a compound of formula (C), and (X) and (C) are:

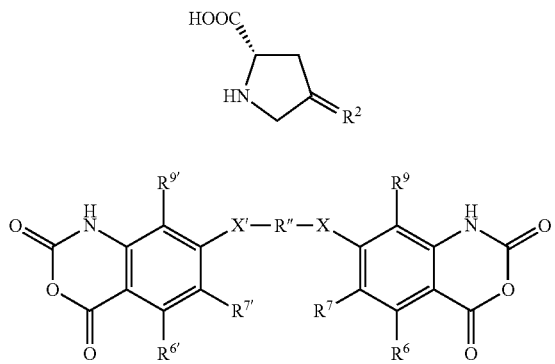

and $R^{6'}$, $R^{7'}$, $R^{9'}$, X', R", $R^2$, $R^6$, $R^7$, $R^9$, and X are as defined above.

22. A process for the preparation of a compound of formula (S), the process comprising the step of reacting (W) with an alkene forming reagent comprising a group $R^2$, wherein the compound of formula (S) is:

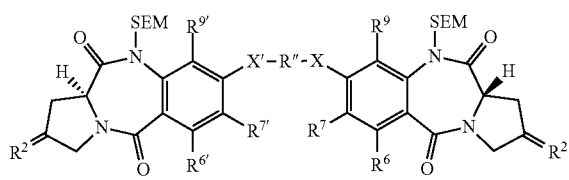

wherein:
SEM is 2-(trimethylsilyl)ethoxymethyl;
$R^2$ is $CHR^{2.4}$, and $R^{2.4}$ is independently selected from H, R, $CO_2R$, COR, CHO, $CO_2H$, and halo;
$R^6$ and $R^9$ are independently selected from H, R, OH, OR, SH, SR, $NH_2$, NHR, NRR', $NO_2$, $Me_3Sn$ and halo;
$R^7$ is independently selected from H, R, OH, OR, SH, SR, $NH_2$, NHR, NRR', $NO_2$, $Me_3Sn$ and halo;
or the adjacent groups $R^6$ and $R^7$ together form a group —O—$(CH_2)_p$—O—, where p is 1 or 2; and
R is independently selected from optionally substituted $C_{1-12}$ alkyl, $C_{3-7}$ heterocyclyl and $C_{5-20}$ aryl groups, wherein the optional substituents are selected from $C_{1-7}$ alkyl, $C_{3-7}$ heterocyclyl, $C_{5-20}$ aryl, halo, hydroxy, $C_{1-7}$ alkoxy, $C_{3-20}$ heterocyclyloxy, and $C_{5-20}$ aryloxy;
R" is a $C_{3-12}$ alkylene group, which chain may be interrupted by one or more heteroatoms selected from O, S and N(H) and/or aromatic rings;
each X is independently selected from O, S, or N(H); and
$R^{2'}$, $R^{6'}$, $R^{7'}$, $R^{9'}$, and X' are independently selected from the same groups as $R^2$, $R^6$, $R^7$, $R^9$, and X respectively; and
wherein $C_{3-7}$ heterocyclyl pertains to a monovalent moiety obtained by removing a hydrogen atom from a ring atom of a heterocyclic compound, which moiety has from 3 to 7 ring atoms, of which from 1 to 4 are ring heteroatoms, selected from N, O and S;
and (W) is a compound:

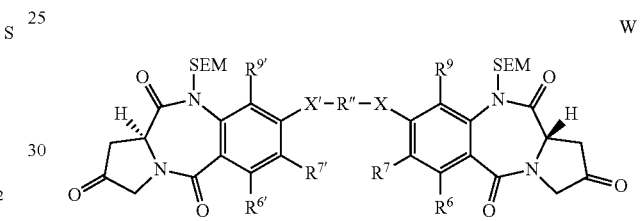

where $R^2$, $R^{6'}$, $R^{7'}$, $R^{9'}$, X', R", $R^6$, $R^7$, $R^9$, and X are as defined for the compound of formula (S).

23. The process according to claim 22, wherein the alkene forming reagent is a phosphonium methylene ylide, and $R^2$ and $R^{2'}$ are each H.

* * * * *

UNITED STATES PATENT AND TRADEMARK OFFICE
CERTIFICATE OF CORRECTION

PATENT NO. : 8,487,092 B2  
APPLICATION NO. : 13/124232  
DATED : July 16, 2013  
INVENTOR(S) : Philip Wilson Howard et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 2 days.

Signed and Sealed this  
Twenty-ninth Day of July, 2014

Michelle K. Lee  
*Deputy Director of the United States Patent and Trademark Office*